(12) United States Patent
Garner et al.

(10) Patent No.: US 8,631,531 B2
(45) Date of Patent: Jan. 21, 2014

(54) APPARATUS AND METHOD FOR BRUSHING TEETH

(76) Inventors: Robert Garner, Miami, FL (US); Heather Brundage, Cambridge, MA (US); Nathaniel Sharpe, Cambridge, MA (US); Alexis Hornstein, Raleigh, NC (US); James Brewster, Miami, FL (US)

( * ) Notice: Subject to any disclaimer, the term of this patent is extended or adjusted under 35 U.S.C. 154(b) by 0 days.

(21) Appl. No.: 13/486,135

(22) Filed: Jun. 1, 2012

(65) Prior Publication Data

US 2013/0014332 A1    Jan. 17, 2013

Related U.S. Application Data

(63) Continuation-in-part of application No. 13/182,414, filed on Jul. 13, 2011.

(51) Int. Cl.
*A61C 17/22* (2006.01)

(52) U.S. Cl.
USPC .......................................... 15/22.1; 15/22.2

(58) Field of Classification Search
USPC .................... 15/22.1, 167.2, 167.1
See application file for complete search history.

(56) References Cited

U.S. PATENT DOCUMENTS

| 5,177,827 A | * | 1/1993 | Ellison ........................... 15/22.1 |
| 7,757,328 B2 | * | 7/2010 | Hegemann et al. ............ 15/22.2 |

* cited by examiner

*Primary Examiner* — Shay Karls
(74) *Attorney, Agent, or Firm* — Allen, Dyer, Doppelt, Milbrath & Gilchrist, P.A.

(57) ABSTRACT

A device and method for brushing all surfaces of all of a user's teeth simultaneously. The device comprises bristle strip surfaces that envelope all of a user's teeth, the bristle strips comprising bristle bundles that scrub all surfaces of a user's teeth due to a reciprocating motion of the bristle strips. To use the device, a user inserts the toothbrush bristle strips into their mouth so to engage the user's teeth. A power source, motor, and drive assembly are utilized to cause the bristles to reciprocate, cleaning all a user's teeth surfaces simultaneously.

23 Claims, 35 Drawing Sheets

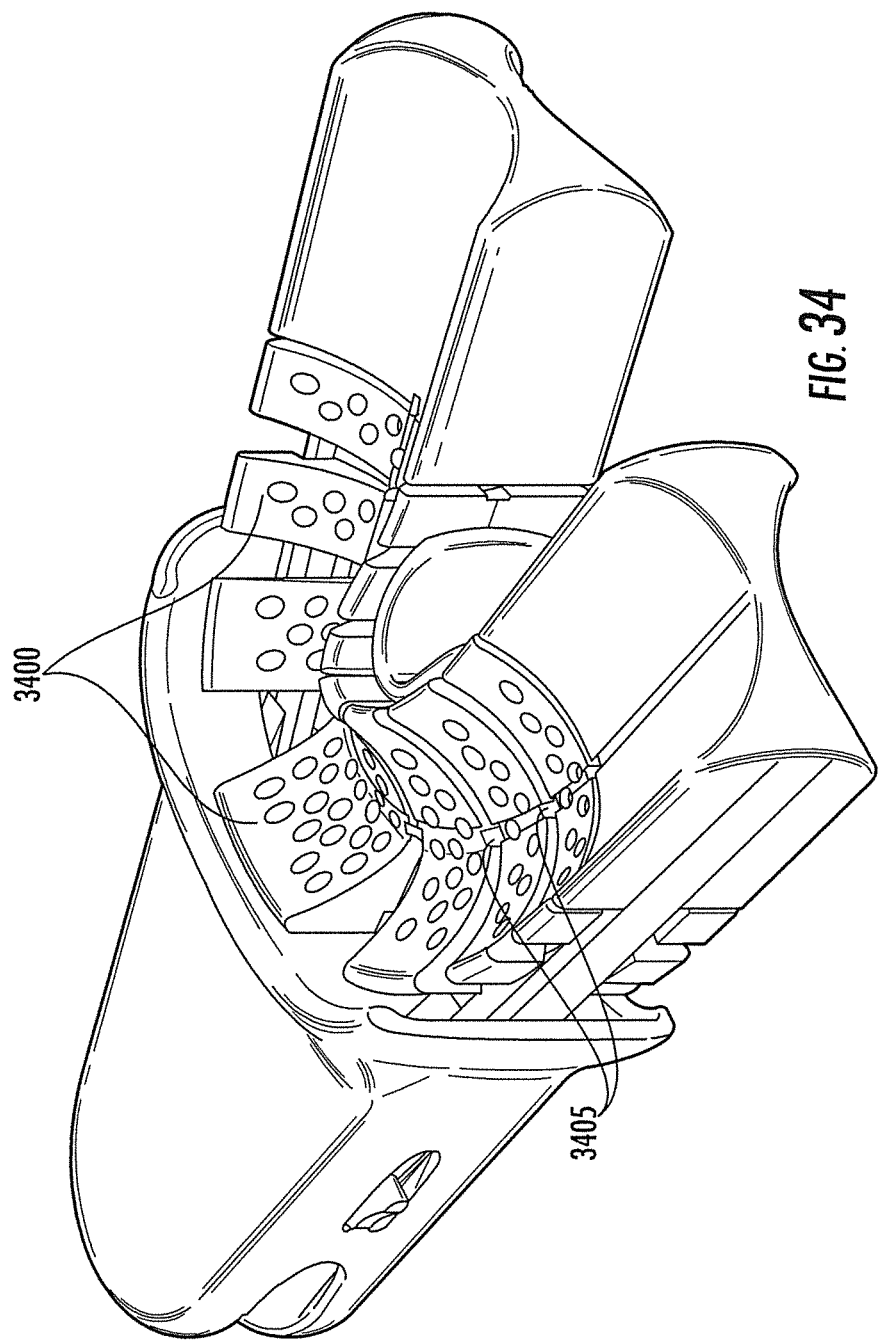

APPARATUS AND METHOD FOR BRUSHING TEETH

CROSS-REFERENCE TO RELATED APPLICATION

This application is a Continuation-in-Part of pending U.S. patent application Ser. No. 13/182,414 filed on Jul. 13, 2011 entitled "Teethbrush," the contents of which are incorporated by reference herein.

FIELD OF THE INVENTION

The present invention relates to a toothbrush that brushes all of a user's teeth simultaneously.

BACKGROUND OF THE INVENTION

The toothbrush is an oral hygiene instrument used to remove plaque, clean teeth, and stimulate the gums. The standard manual toothbrush consists of a bristled head attached to a handle, wherein the bristled head is only capable of cleaning a small area at a time. The recommended way to manually brush teeth is to use the Bass method, whereby the toothbrush is held such that the bristles are angled at a 45° angle to the long axis of the tooth and moved back and forth in short, quick strokes. This motion requires a certain level of manual dexterity often absent in the very young, the elderly, and people with physical or mental limitations. Additionally, it is the user's responsibility to ensure that each tooth surface is adequately cleaned. Since this is difficult to determine, it is recommended that a person should brush for at least two minutes to effectively clean all the surfaces of his or her teeth. Unfortunately, many people do not have a convenient or accurate way to time their brushing routine, so do not realize how long they have actually been brushing, thus resulting in shorter brushing sessions that fail to adequately remove plaque from all surfaces. Additionally, the time spent brushing each tooth is often distributed unevenly, so that some teeth get more attention than others.

An electric toothbrush uses electric power to either move individual bristles ultrasonically or to rapidly move a brush head. Electric toothbrushes augment the normal brushing capabilities of a person, and some electric toothbrushes even include a timer feature and/or automatically turn off after a predetermined amount of time to indicate to the user when the appropriate amount of brushing time has lapsed. Although this helps encourage longer brushing times, many users still do not brush for long enough in spite of these aids. Though these capabilities encourage proper brushing, standard electric toothbrushes still require a user to move the toothbrush from tooth to tooth and to manipulate the toothbrush onto the various surfaces of each tooth. As with a manual toothbrush, a person with limited manual dexterity may find using an electric toothbrush difficult or impossible because of the manipulation required to properly reach every tooth surface. This also does not solve the problem of favoring certain teeth or regions of teeth over other teeth or other regions of teeth.

The Hydrabrush® (a.k.a. "30 Second Smile") is a multi-head brush that engages upper and lower teeth simultaneously. This toothbrush, however, only engages a small number of teeth at any given moment, thus still necessitating a high level of manual dexterity to properly manipulate the handle. Additionally, since the Hydrabrush® only engages a small number of teeth simultaneously, the time duration necessary to adequately clean all of a user's teeth is still relatively high, as is the likelihood that a user will favor certain tooth regions.

Regardless of whether a person uses a manual or an electric toothbrush, a person who is rushed, too tired, or physically or mentally impaired may not spend the recommended time brushing his or her teeth. Additionally, he or she may also not be willing or able to adequately manipulate the toothbrush in a manner to effectuate adequate brushing. These deficiencies could result in substandard oral hygiene, potentially risking dental caries and gum disease.

SUMMARY OF THE INVENTION

Embodiments of the present invention address a full mouth toothbrush that engages substantially all of a user's teeth simultaneously comprising at least one actuatable bristle strip of a size and dimension to substantially engage a user's teeth. A substantially U-shaped frame of a size and dimension to fit in a user's mouth engages at least one bristle strip. An actuation means in communication with the bristle strip imparts a reciprocating motion to the bristle strip, and an aperture within the frame allows the bristle strip to communicate with the actuation means. A motor engages the actuation means, and a power source provides power to the motor.

In one embodiment of the invention, a full mouth toothbrush comprises at least one actuatable bristle strip of a size and dimension to substantially engage a user's teeth with at least one rigid beam attaching to the bristle strip. This rigid beam comprises a projection that extends outwardly from the bristle strip to engage an actuation means. The actuation means comprises a gear train having reciprocating pins in communication with the rigid beam projection. A motor engages the actuation means, and a power source provides power to the motor.

In another embodiment, a full mouth toothbrush comprises a semi-elliptical, actuatable, upper bristle strip comprising an upper surface that is adapted to envelope the upper teeth of a subject, wherein a plurality of bristle bundles engages the upper surface of the upper bristle strip. Additionally, a semi-elliptical, actuatable, lower bristle strip comprises a lower surface, the lower surface adapted to enveloping the lower teeth of a subject, wherein a plurality of bristle bundles engages the lower surface of the lower bristle strip. An actuation means is in communication with at least one bristle strip, the actuation means capable of reciprocatingly actuating the bristle strip. At least one rigid beam attaches to at least one bristle strip, the rigid beam comprising a projection extending outwardly from the bristle strip to engage an actuation means. Additionally, an actuation means comprises a gear train having reciprocating pins that are in communication with the rigid beam projection. A motor engages the actuation means, and a power source provides power to the motor.

BRIEF DESCRIPTION OF THE DRAWINGS

For a fuller understanding of the invention, reference is made to the following detailed description, taken in connection with the accompanying drawings illustrating various embodiments and principles of the present invention. The embodiments illustrated herein are presently preferred, it being understood, however, that the invention is not limited to the precise arrangements and instrumentalities shown, wherein:

FIG. 31b illustrates an isometric view of the bristle strip of FIG. 31a;

FIG. 34 illustrates an isometric view of the hinged bristle strip assembly of a non-framed rigid beam mouthpiece of FIG. 33;

FIG. 35b illustrates an isometric view of the bristle strip of FIG. 35a;

FIG. 36b illustrates an isometric view of the mouthpiece of FIG. 36a.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The Handle and Base

This invention teaches a full mouth toothbrush which allows the brushing of multiple teeth simultaneously. Through use of the full mouth toothbrush, little or no user intervention is required to clean multiple surfaces of multiple teeth simultaneously after the full mouth toothbrush is placed in the mouth of a user. This affords a user with limited dexterity, or someone with limited time or energy, to receive an effective cleaning of his/her teeth for improved dental hygiene.

Figure 1:
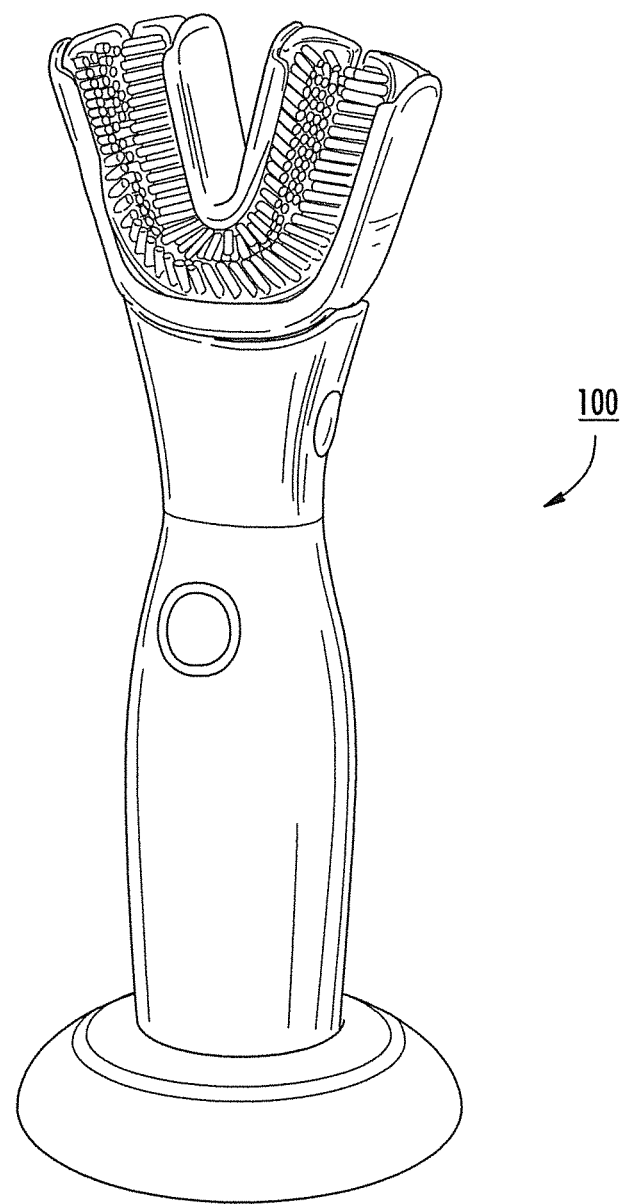
FIG. 1 illustrates an isometric view of the apparatus.
Figure 2:
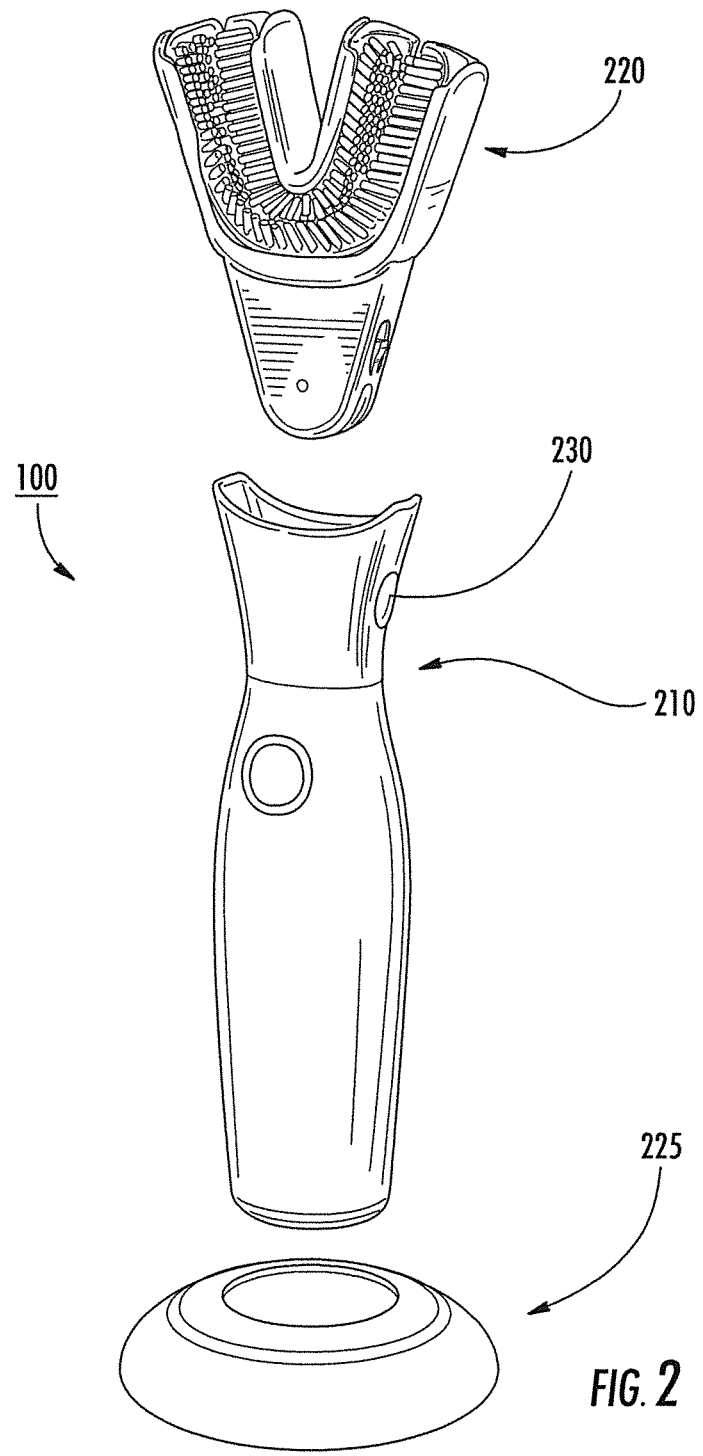
FIG. 2 illustrates an exploded isometric view of the apparatus.

Referring initially to FIG. 1, by way of example, one embodiment contemplated by the invention for the full mouth toothbrush 100 (also referred to as "device" or just "toothbrush") comprises several main components as illustrated in FIG. 2. In particular, FIG. 2 illustrates an example of a multipart toothbrush 100 construction comprising a handle 210, the handle communicating with a mouthpiece 220, and a charging base 225 in which the handle fits for purposes of recharging and/or storing the toothbrush 100. In this embodiment of the toothbrush 100, the mouthpiece 220 can be disengaged from the handle 210 to clean and/or replace a worn mouthpiece 220.

As illustrated by FIG. 2, the mouthpiece 220 is ejected from the handle 210 using at least one ejection button 230. This further allows a multitude of users to insert a personal mouthpiece 220 into the handle 210 for use of the device 100. The handle 210 is not limited to a specific build, make, or model—nor is it limited to a particular ergonomic shape. However, in this embodiment, the handle 210 is capable of accepting and later removing the mouthpiece 220. Other embodiments (not shown), however, contemplate a unibody construction such that the mouthpiece 220 is rigidly engaged to the handle 210.

Certain embodiments of the invention contemplate use of the mouthpiece 220 without use or need for a handle 210. Likewise, the invention contemplates a handle 210 which does not require a power source or a motor assembly (described in detail below).

Figure 3:
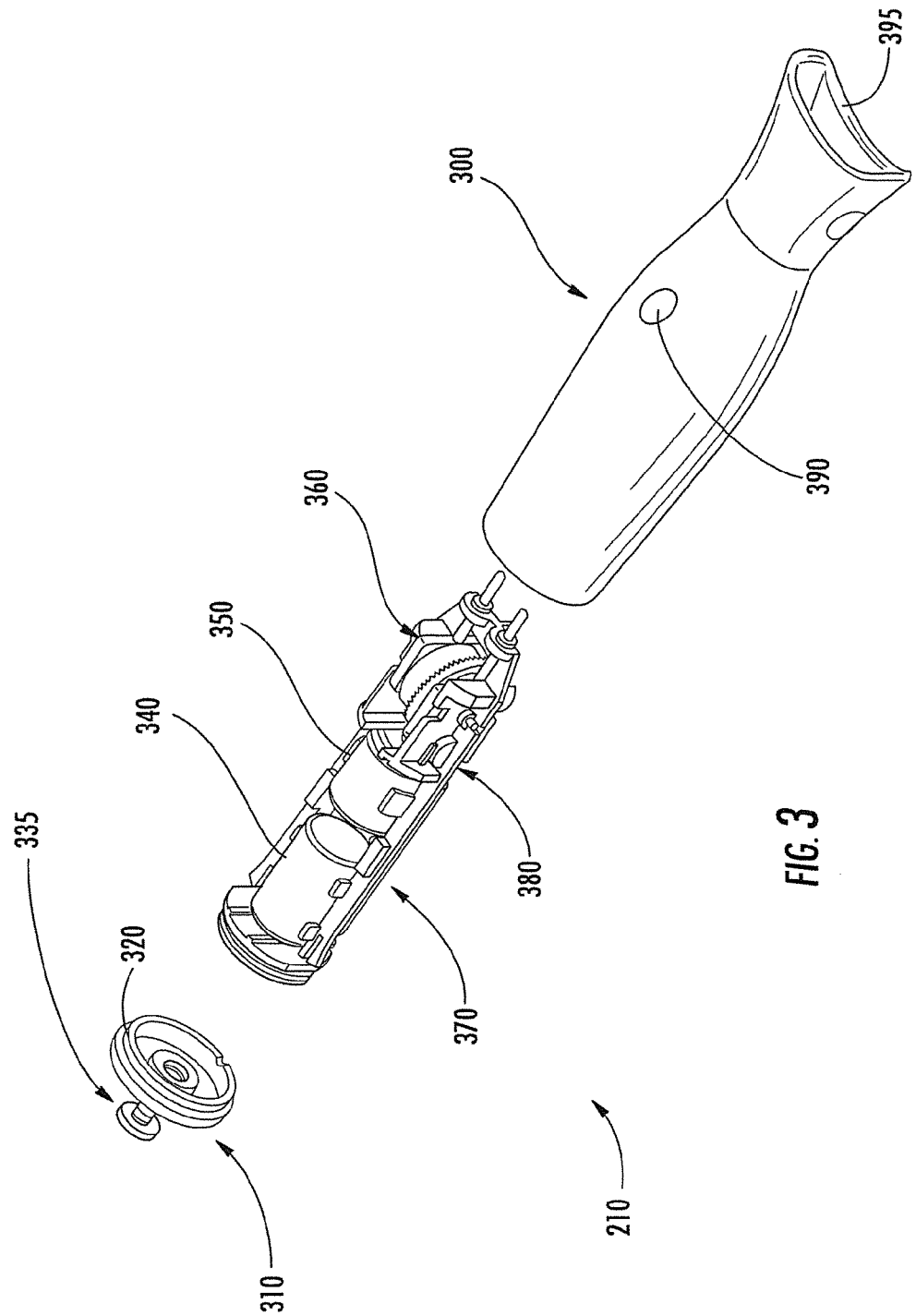
FIG. 3 illustrates an exploded isometric view of an embodiment of the apparatus indicating internal components.

Referring to FIG. 3, in one embodiment, the handle 210 comprises a handle shell 300, the shell having an end cap 310 that seals the components inside the handle shell 300 from the elements. A cap seal 320 maintains a water-tight connection between the handle shell 300 and the end cap 310. In one embodiment, the cap seal 320 is an o-ring. The end cap 310 is threaded, and engages complimentary threads of the handle shell 300. In another embodiment, the end cap 310 is secured to the handle shell 300 with a fastener 335 which is connected to the chassis 370.

With continuing reference to FIG. 3, the handle shell 300 houses a battery 340 that powers a motor 350. The motor 350 actuates a gear train 360, the gear train 360 communicating with the mouthpiece 220. The battery 340, motor 350, and gear train 360 are mounted to a chassis 370 that engages the handle shell 300. In one embodiment, the chassis 370 also houses a desiccant 380 for the purpose of reducing moisture levels within the handle shell. When in non-use, the toothbrush 100 may rest in the charging base 225 for the purpose of recharging the battery 340.

The handle shell 300 further comprises a power button 390. The power button 390 is not limited to a button, but can be a switch or similar device. In one embodiment, the charging base 225 has a power cord that plugs into an electrical outlet, which serves to provide power to recharge the battery 340. In this embodiment, the charging base 225 wirelessly transmits energy through an induction charging coil and through the handle 210, to store energy in the battery 340. In another embodiment, the full mouth toothbrush 100 comprises electrical contacts that contact mating contacts in the charging base 225 for the purpose of recharging the battery 340. In another embodiment, the base 140 serves as a toothbrush 100 holder. The handle shell 300, end cap 310, chassis 370, and charging base 225 are each made from a material chosen from the group consisting of high density polyethylene, low density polyethylene, polyethylene terephthalate, polyvinyl chloride, polypropylene, polyoxymethylene, polystyrene, post-consumer resin, K-resin, epoxy resin, phenolic formaldehyde resin, stainless steel, aluminum, ceramic, wood, metal, and any other material known in the art. The preferred materials for the handle shell 300, end cap 310, chassis 370, and charging base 225 are polymeric alloys suitable for injection-molding.

As further illustrated in FIG. 3, the handle shell 300 can comprises a mouthpiece gasket 395 for the purpose of maintaining an essentially secure fit between the handle shell 300 and the mouthpiece 220. In one embodiment, the gasket 395 is made of plastic. In an alternative embodiment, the gasket 395 is made of a low durometer material (such as rubber or silicone) so to compress slightly upon the inserting of the mouthpiece 220 into the handle 210 to foster the creation of a seal.

Framed Mouth Piece

Figure 4:
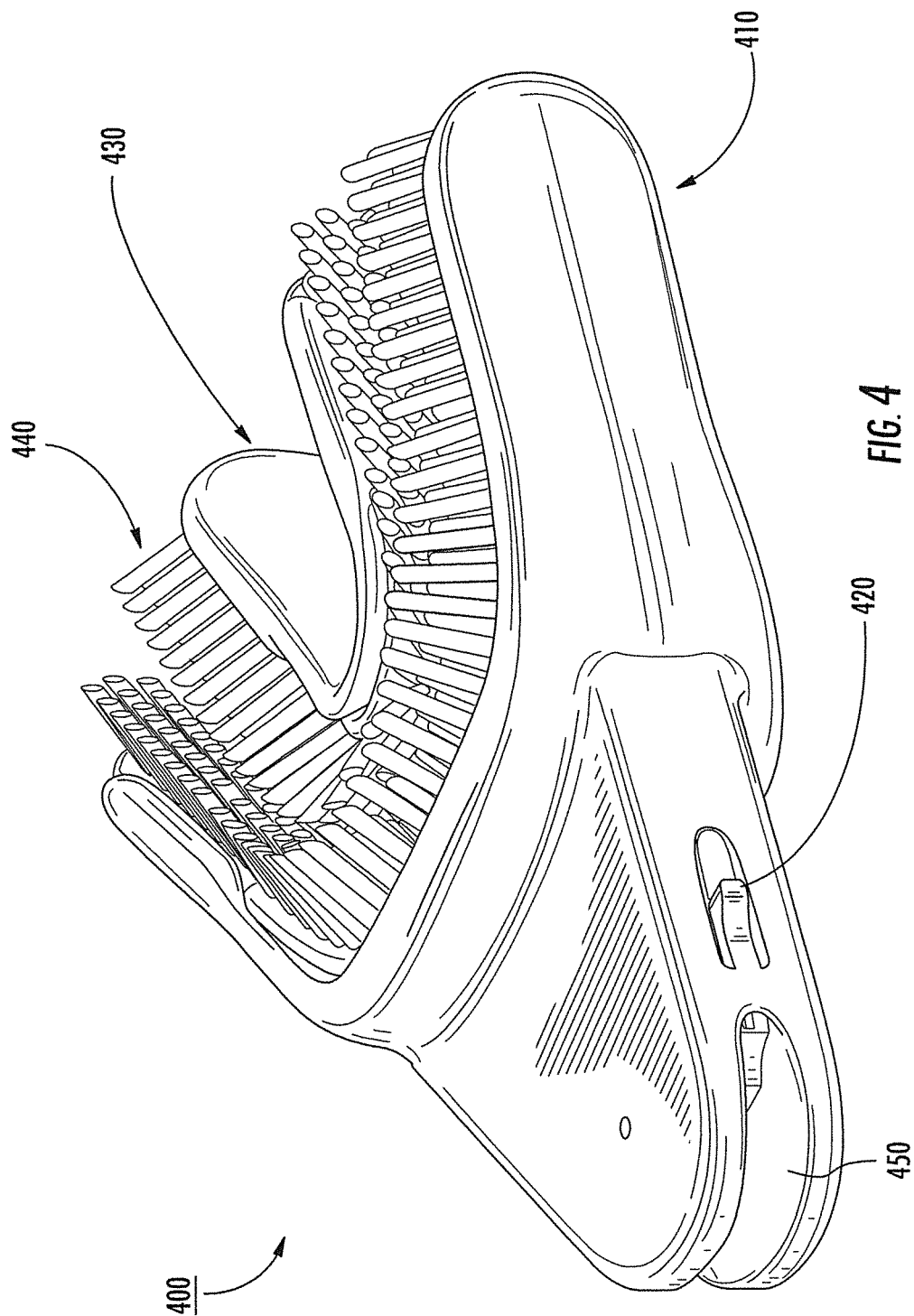
FIG. 4 illustrates an isometric view of an embodiment of a framed mouthpiece.
Figure 5:
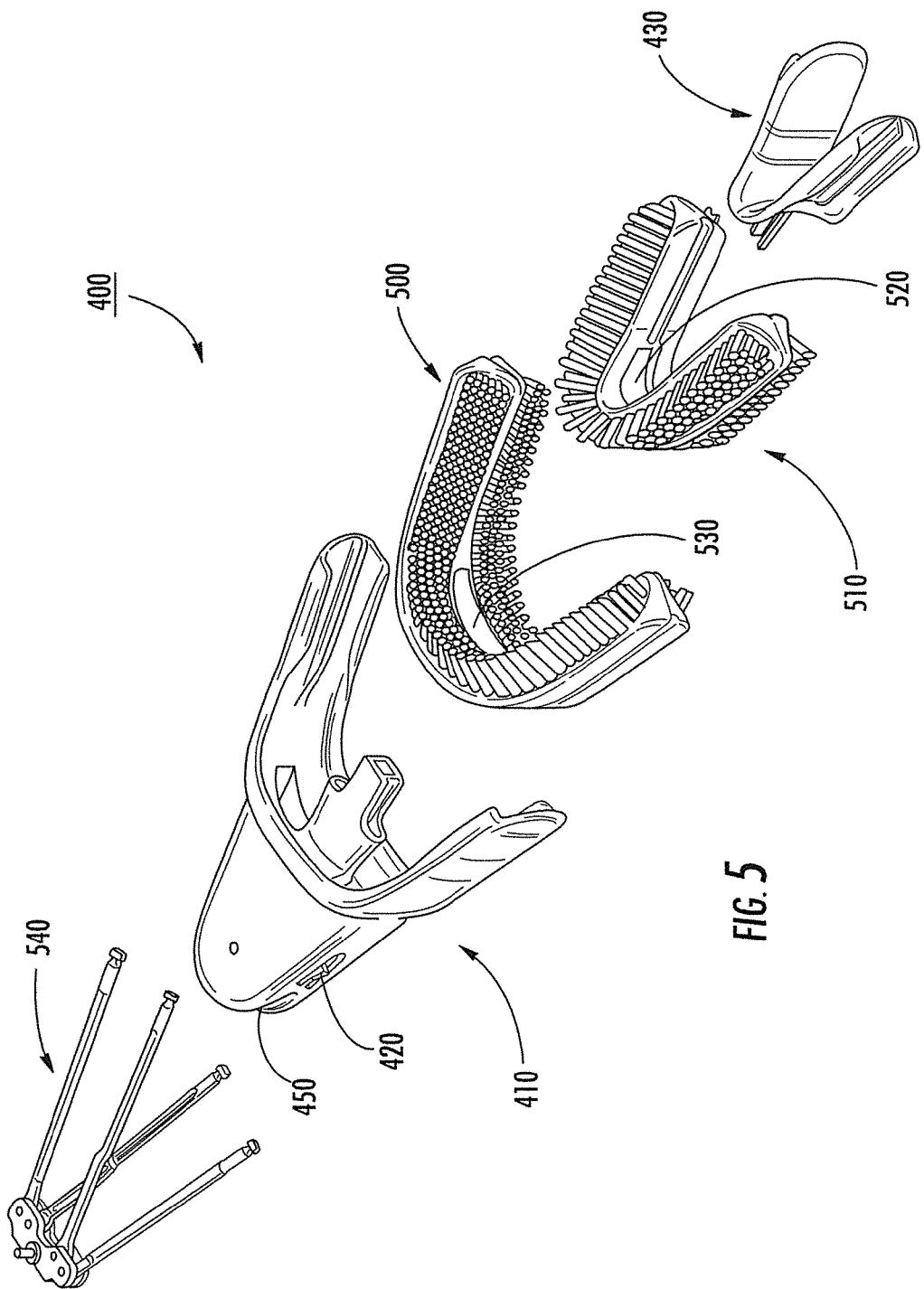
FIG. 5 illustrates an exploded isometric view of an embodiment of a framed mouthpiece.

FIG. 4 illustrates an embodiment of the mouthpiece 220, referred to as a framed mouthpiece 400. An outer frame 410 of the framed mouthpiece 400 engages the handle 210. A snap hook 420 on the outer frame 410 attaches the outer frame 410 (and therefore the entire assembled mouthpiece 400) to the handle 210, engaging at least one eject button 230 on the handle 210. An inner frame 430 engages the outer frame 410, and sandwiches bristle strips (more fully described below and more fully illustrated in FIG. 5) between the inner frame 430 and outer frame 410. The framed mouthpiece 400 is of a size and dimension so to fit in a user's mouth and allow bristle bundles 440 to engage substantially all the surfaces of substantially all the user's teeth. As illustrated in FIG. 4 and FIG. 5, the outer frame 410 comprises an aperture 450 proximate the end of the outer frame that engages the handle 210. The aperture 450 provides a means for a drive system 540 to engage outer 500 and inner 510 bristle strips.

FIG. 5 more fully illustrates the embodiment of the framed mouthpiece 400 illustrated in FIG. 4. An outer bristle strip 500 engages the outer frame 410. An inner bristle strip 510 engages the inner frame 430. Upon assembly of the framed mouthpiece 400, the inner frame 430 fixedly engages the outer frame 410, passing through an inner bristle strip aperture 520, and an outer bristle strip aperture 530, and flanks the inner bristle strip 510 and the outer bristle strip 500 between the inner frame 430 and the outer frame 410. In one embodiment, a bristle strip assembly comprises the outer 500 and inner 510 bristle strips within a framed mouthpiece 400. Both the outer bristle strip 500 and the inner bristle strip 510 are of a substantially semi-elliptical shape adapted to follow the contours of a set of teeth. The bristle strips 500, 510 are made from at least one of high density polyethylene, low density polyethylene, polyethylene terephthalate, polyvinyl chloride, polypropylene, ABS, polyoxymethylene, polystyrene, post-consumer resin, K-resin, epoxy resin, phenolic formaldehyde resin, stainless steel, aluminum, titanium, ceramic, and any other material known in the art. In a preferred embodiment, the bristle strips 500, 510 are made of a thermoplastic elastomer. The substantially semi-elliptical inner bristle strip 510 nests substantially within the substantially semi-elliptical outer bristle strip 500, and forms at least one, and preferably two, substantially semi-elliptical channels of a suitable size and dimension to substantially envelope a set of teeth. In a preferred embodiment, an upper channel engages the upper teeth and a lower channel engages the lower teeth. The bristle strips 500, 510 comprise a plurality of bristle bundles 440 projecting from an inner surface of the channel.

The bristle bundles 440 of the inner bristle strip 510 engage both the upper and lower lingual, occlusal, and incisal teeth surfaces. The bristle bundles 440 of the outer bristle strip 500 engage both the upper and lower facial, occlusal, and incisal teeth surfaces. In combination, the bristle bundles 440 of the bristle strips 500, 510 are designed to engage and clean all teeth surfaces simultaneously. Different sizes and shapes of the bristle strips 500, 510 are contemplated to accommodate a variety of mouth shapes and sizes. Offsetting the upper and lower channels can accommodate individuals with either an underbite or overbite.

Gear Train

Figure 6:
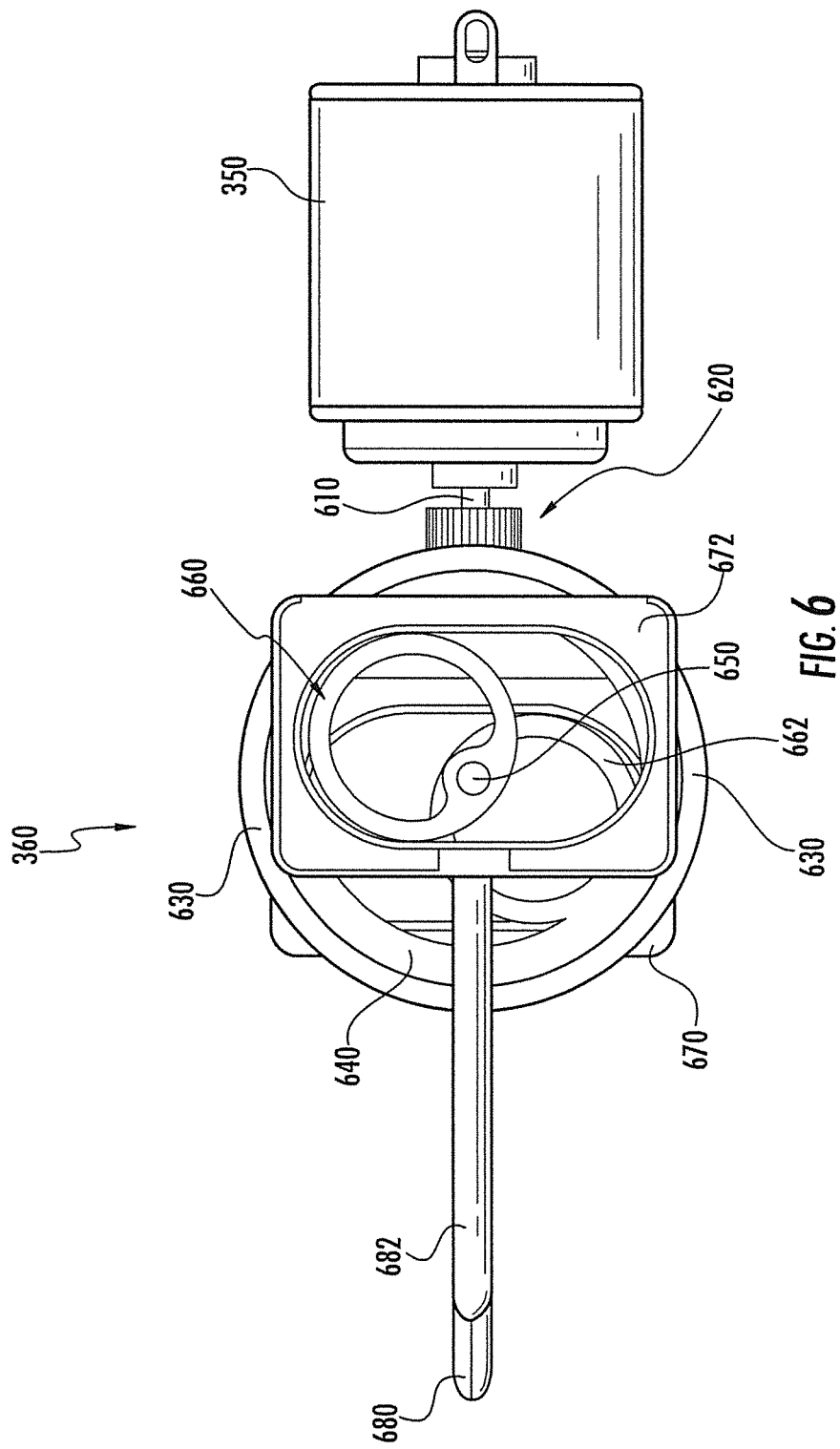
FIG. 6 illustrates a side view of an embodiment of a drive train.
Figure 7:
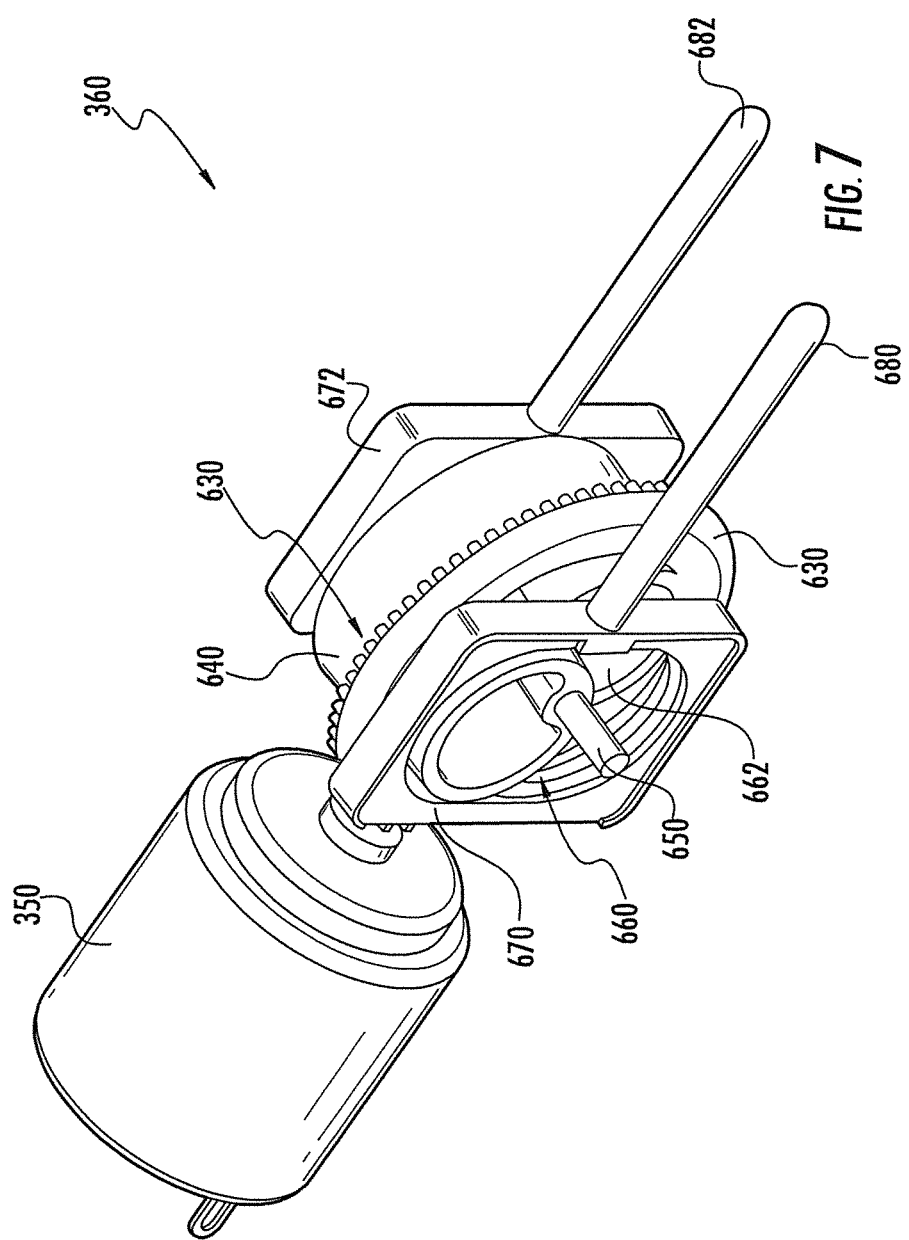
FIG. 7 illustrates an isometric view of an embodiment of the drive train of FIG. 6.
Figure 8:
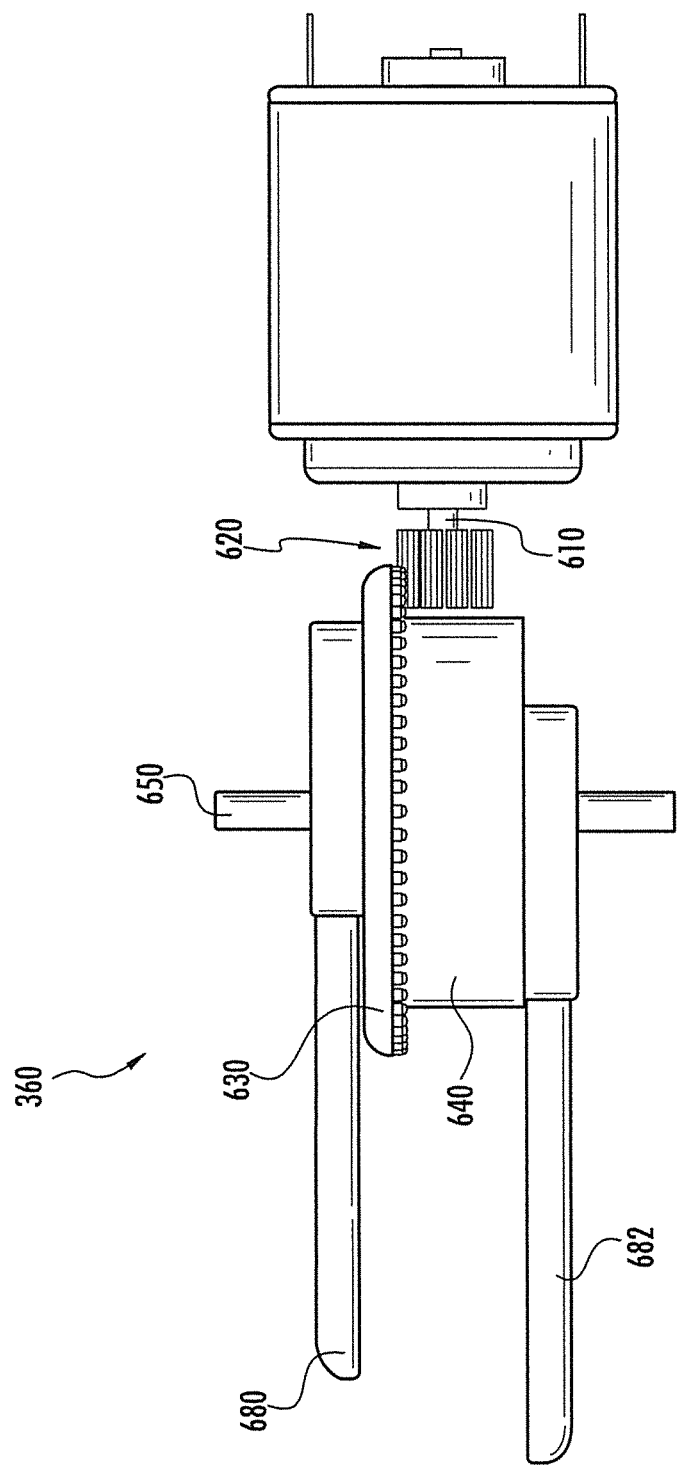
FIG. 8 illustrates a top view of an embodiment of the drive train of FIG. 6.

FIGS. 6, 7 and 8 illustrate, by way of example, an embodiment of a gear train 360. In this embodiment, an armature 610 of the motor 350 fixedly engages a spur gear 620. The spur gear 620 engages a perpendicular face gear 630. In one embodiment, the face gear 630 comprises a cylinder 640. The cylinder rotates along with the face gear 630 around an axle 650. Attached or molded to the cylinder are two cams, a first cam 660 and a second cam 662, each cam 660, 662 being situated opposite to each other by approximately 180° perpendicular the cylinder's 640 rotational axis. The cams 660, 662 are each offset from the cylinder 640, protruding outwardly from the interior of the cylinder 640 parallel to the rotational axis.

The first cam 660 communicates with a first cam follower 670. The second cam 662 communicates with a second cam follower 672. The first cam follower 670 communicates with a first reciprocating pin 680, and the second cam follower 672 communicates with a second reciprocating pin 682. In the preferred embodiment, each cam follower 670, 672 is made of plastic, overmolded onto each stainless steel reciprocating pin 680,682. In another embodiment, the reciprocating pin 680,682 and cam follower 670, 672 are a single piece of molded plastic.

When the armature 610 of the motor 350 rotates, the spur gear 620 fixedly rotates with the armature 610, rotating the face gear 630 and the cylinder 640 around the axle 650. This actuates the eccentric paths of the first cam follower 670 and the second cam follower 672, causing a reciprocation of the first and second reciprocating pins 680, 682, respectively, thereby translating a rotational motion of the cams 660, 662, to a linear reciprocation of the reciprocating pins 680, 682. These reciprocating pins 680, 682 engage a drive system, as described below.

Drive System: Wire Drive

It should be noted that this description discloses a plurality of drive mechanism variations as well as a plurality of bristle strip variations. Combinations between specific embodiments of drive mechanisms interacting with embodiments of bristle strips are disclosed for illustrative purposes, and combinations not specifically disclosed are contemplated by this invention nonetheless.

Figure 9:
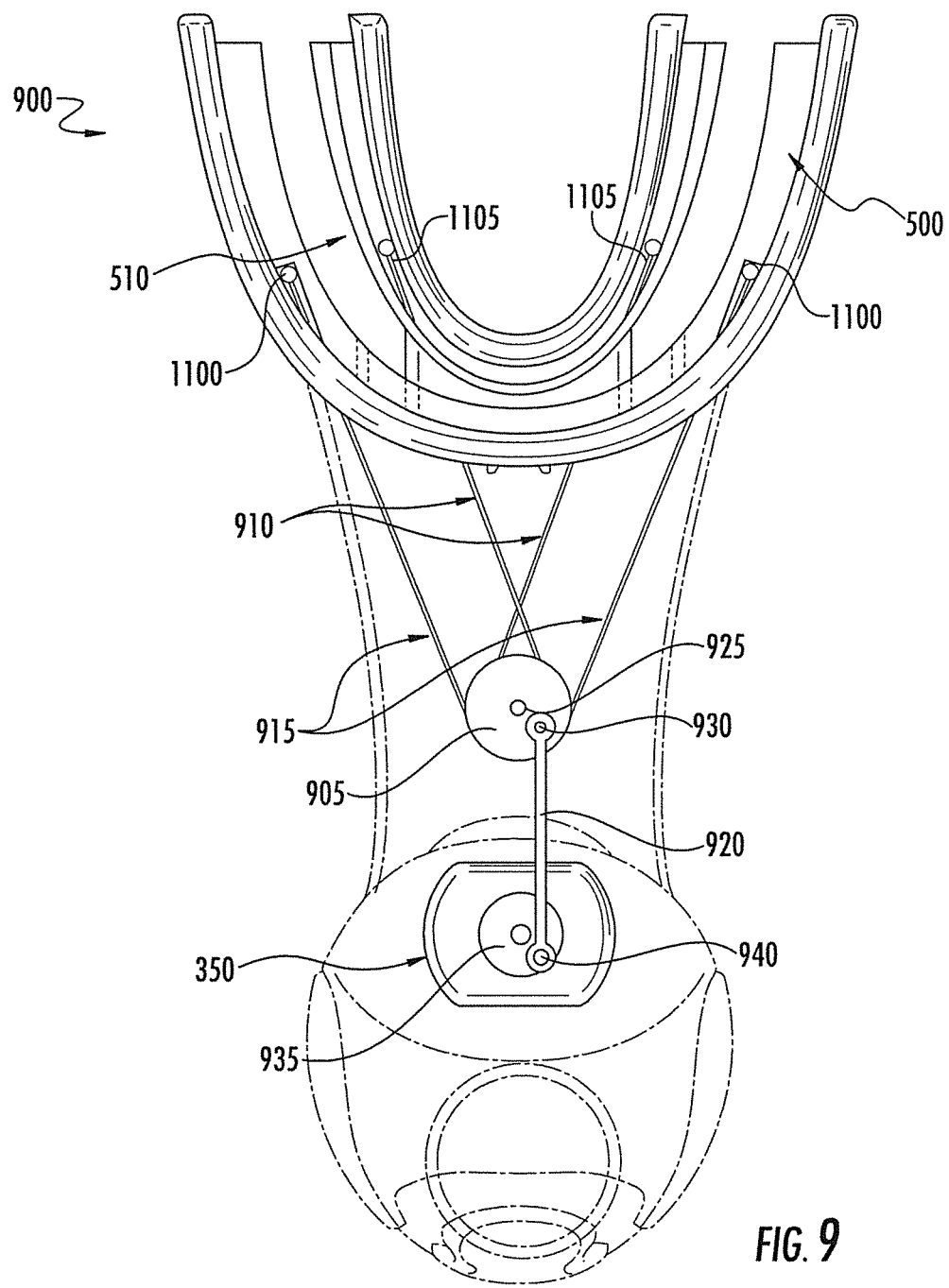
FIG. 9 illustrates a top cutaway view of an embodiment of the wire drive assembly.

FIG. 9 illustrates, by way of example, an embodiment of a wire drive assembly 900 wherein a pulley 905 engages drive wires—an inner drive wire 910 and an outer drive wire 915. The pulley 905 reciprocates, and this reciprocating motion is communicated to the bristle strips 500, 510 via the drive wires 910, 915. A rocker linkage 920 pivotally communicates with the pulley 905. The pulley 905 is pivotally mounted to a central shaft 925. The central shaft 925 freely rotates around the central shaft's 925 long axis. In one embodiment, the central shaft 925 communicates with at least one of a bushing and a bearing. In one embodiment, the rocker linkage 920 engages a wrist pin 930 located peripherally on the pulley 905. In another embodiment, the rocker linkage 920 engages the pulley 905 at a ball-and-socket joint.

The rocker linkage 920 also communicates with a drive wheel 935. In one embodiment, the rocker linkage 920 engages a second wrist pin 940 located peripherally on the drive wheel 935. In another embodiment, the rocker linkage 920 engages the drive wheel 935 at a ball-and-socket joint. The drive wheel 935 rotates when the motor 350 is activated, causing the wrist pin 940 to rotate, which causes the rocker linkage 920, by virtue of being pivotally attached to the pulley 905, to force the pulley 905 to reciprocate about the central shaft 925.

Figure 10:
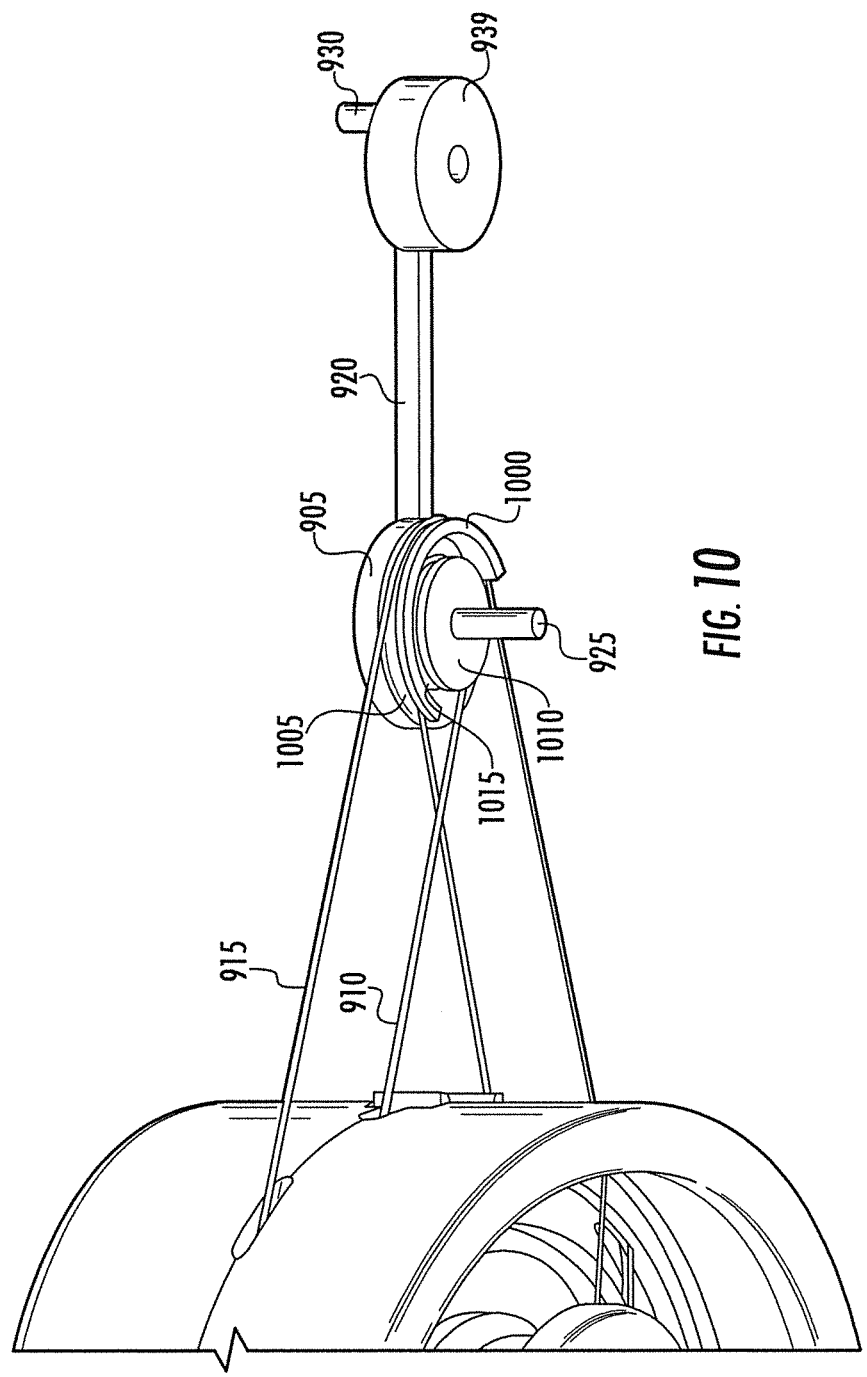
FIG. 10 illustrates an isometric view of an embodiment of the wire drive assembly of FIG. 9.

Turning to FIG. 10, which is another view of the wire drive mechanism of FIG. 9, the pulley 905 comprises at least one externally grooved substantially circularly arched rail 1000 having a shape and dimension to engage the outer drive wire 915. The distal face of the rail 1005 comprises a groove 1005 traversing the length of the rail 1000. The groove 1005 captures the outer drive wire 915 under tension so that when the pulley 905 reciprocates, that reciprocating motion is transferred to the drive wire 915. In one embodiment, the groove surface 1005 is textured to provide more friction to aid in gripping the drive wire 915 without slippage. In one embodiment, the groove 1005 surface is ridged to provide more friction to aid in gripping the drive wire 915 without slippage.

In one embodiment, the groove surface 1005 is lined with a material, such as rubber, to provide more friction to aid in gripping the drive wire 915 without slippage.

The pulley 905 comprises a circular boss 1010, the boss 1010 comprising a second groove 1015 that circumscribes the boss 1010. The second groove 1015 captures the inner drive wire 910 under tension so that when the pulley 905 reciprocates, that reciprocating motion is transferred to the inner drive wire 910. In one embodiment, the second groove's 1015 surface is textured to provide more friction to aid in gripping the inner drive wire 910 without slippage. In one embodiment, the second groove's 1015 surface is ridged to provide more friction to aid in gripping the inner drive wire 910 without slippage. In one embodiment, the second groove's 1015 surface is lined with a material, such as rubber, to provide more friction to aid in gripping the inner drive wire 910 without slippage. The drive wires 915, 915 are made from at least one of metal, natural fibers, synthetic materials such as plastic monofilament, and any materials known in the art.

Figure 11:
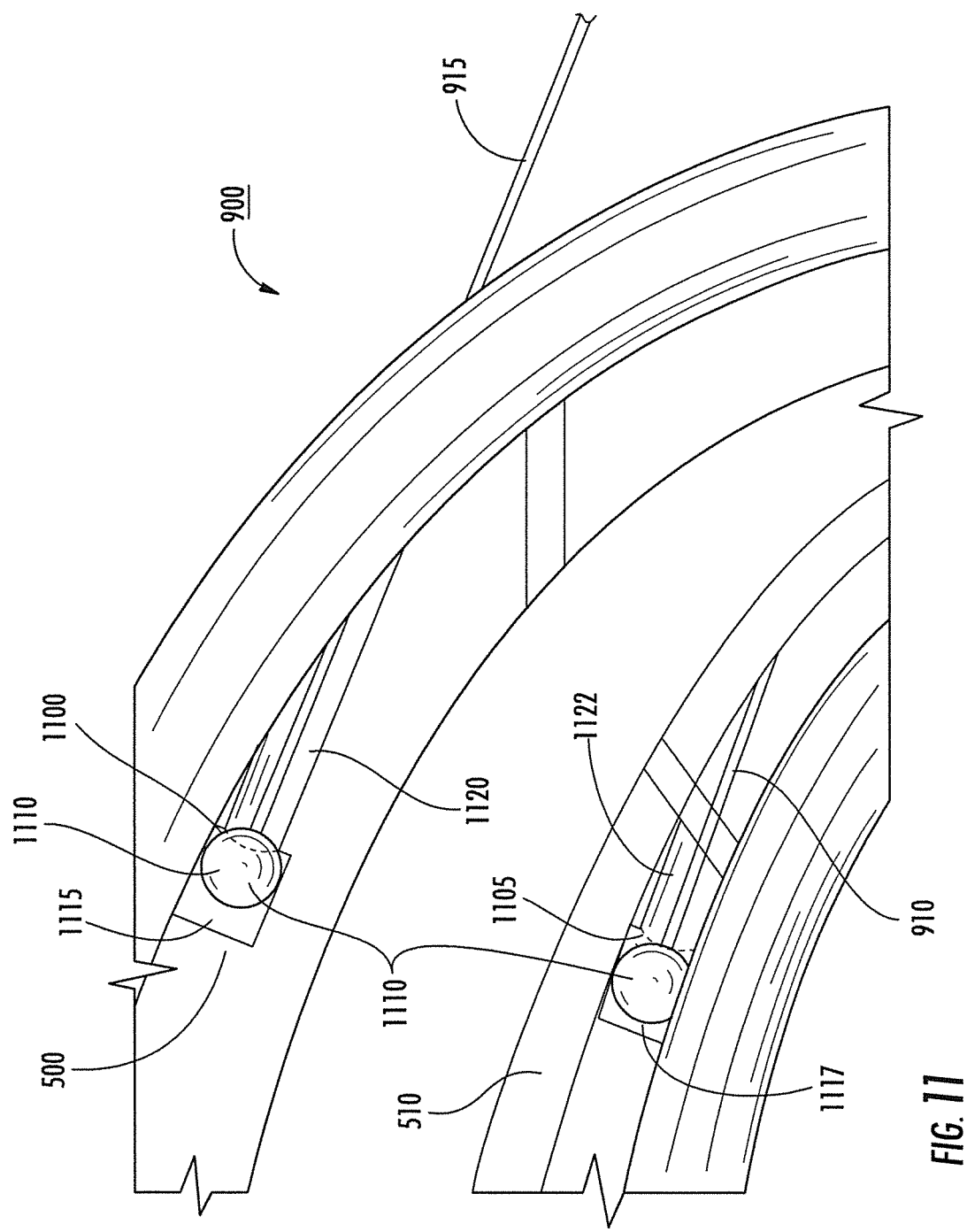
FIG. 11 illustrates a top cutaway view of an embodiment of the wire drive assembly of FIG. 9.

FIG. 11 further illustrates an embodiment of the wire drive system 900. The drive wires 910, 915 communicate with a bristle strip 500, 510 so to cause the bristle strips 500, 510 to reciprocate. In particular, the outer drive wire 915 terminates at opposed attachment points 1100 anchored in the outer bristle strip 500. The inner drive wire 910 terminates at opposed attachment points 1105 anchored in the inner bristle strip 510.

With continuing reference to FIG. 11, the outer drive wire's 915 two attachment points 1100 alternately pull the opposing regions of the outer bristle strip 500 during every reciprocation of the pulley 905. The inner drive wire's 910 two attachment points 1105 alternately pull the opposing regions of the inner bristle strip 510 during every reciprocation of the pulley 905. The attachment points 1100, 1105 comprise a termination 1110, being at least one of spheres, crimps, tubes, hooks, and loops that are at least one of glued, crimped, tied, and welded to each drive wire 910, 915. The relatively large termination 1110 is trapped in a cavity 1115, 1117 of a suitable size and dimension to encase the termination 1110, so the termination 1110 is too large to pass through a channel 1120, 1122 in the bristle strip 500, 510, the channel 1120, 1122 however being large enough to accommodate a drive wire 910, 915.

Referring again to FIG. 10, in one embodiment, the inner drive wire 910, is crossed over itself so that each time the pulley pulls against the wires 910, 915, the wires pull on opposed termination points 1100, 1105 within the bristle strips 500, 510.

Drive System: Linkage Drive

Figure 12:
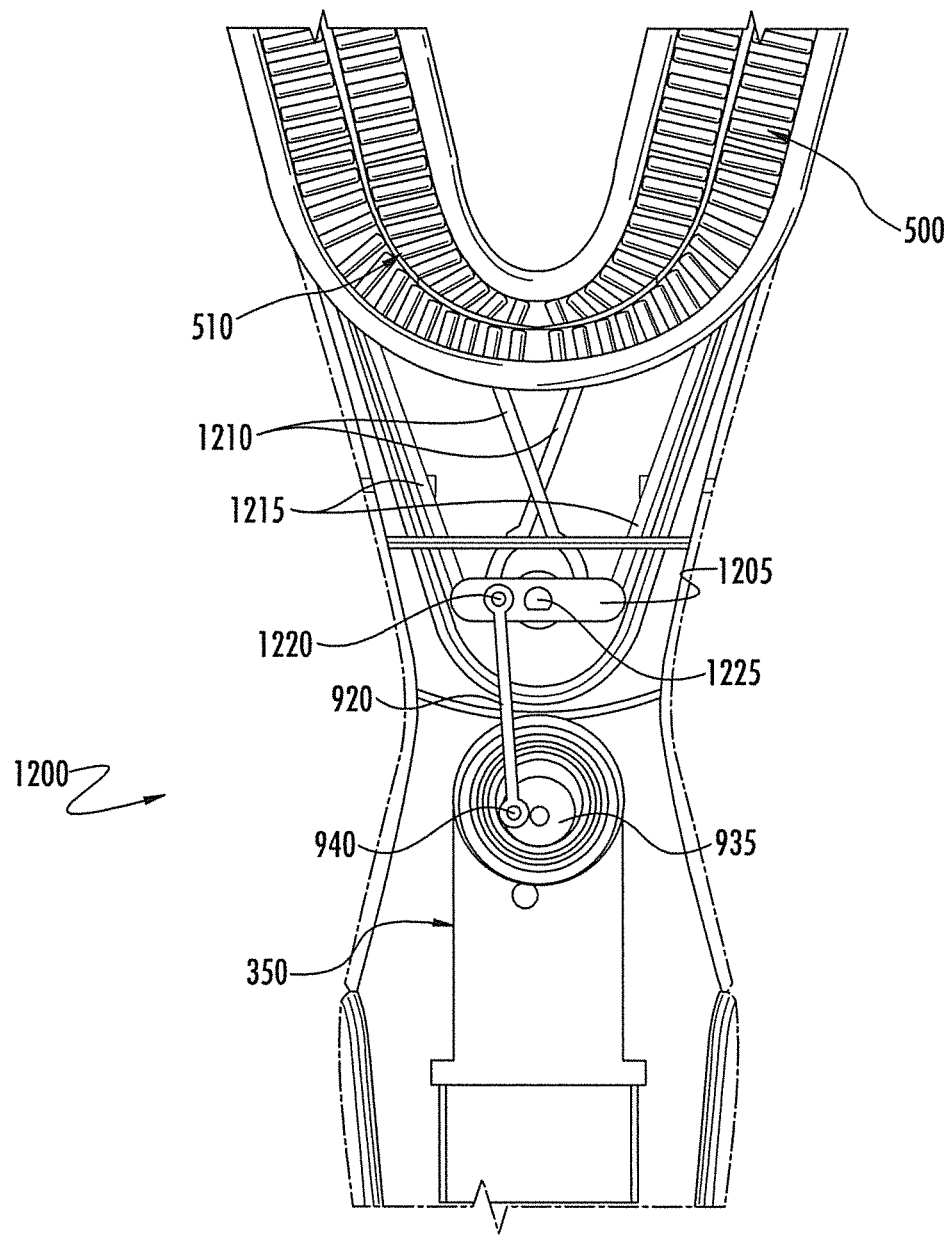
FIG. 12 illustrates a top cutaway view of an embodiment of the linkage drive assembly.

FIG. 12 illustrates, by way of example, an embodiment of a linkage drive assembly 1200 wherein a pivot bar 1205 engages a plurality of drive linkages, inner drive linkages 1210 and outer drive linkages 1215. The pivot bar 1205 reciprocates, and this reciprocating motion is communicated to the bristle strips 500, 510 via the drive linkages 1210, 1215. A rocker linkage 920 pivotally communicates with the pivot bar 1205. The pivot bar 1205 is pivotally mounted to a central shaft 1225. The central shaft 1225 freely rotates around the central shaft's 1225 long axis. In one embodiment, the central shaft 1225 communicates with at least one of a bushing and a bearing. In one embodiment, the rocker linkage 920 engages a wrist pin 1220 located peripherally on the pivot bar 1205. In another embodiment, the rocker linkage 920 engages the pivot bar 1205 at a ball-and-socket joint.

The rocker linkage 920 also communicates with a drive wheel 935. In one embodiment, the rocker linkage 920 engages a second wrist pin 940 located peripherally on the drive wheel 935. In another embodiment, the rocker linkage 920 engages the drive wheel 935 at a ball-and-socket joint. The drive wheel 935 rotates when the motor 350 is activated, which causes the rocker linkage 920, by virtue of being pivotally attached to the wrist pin 940, to force the pivot bar 1205 to reciprocate about the central shaft 1225.

Figure 13:
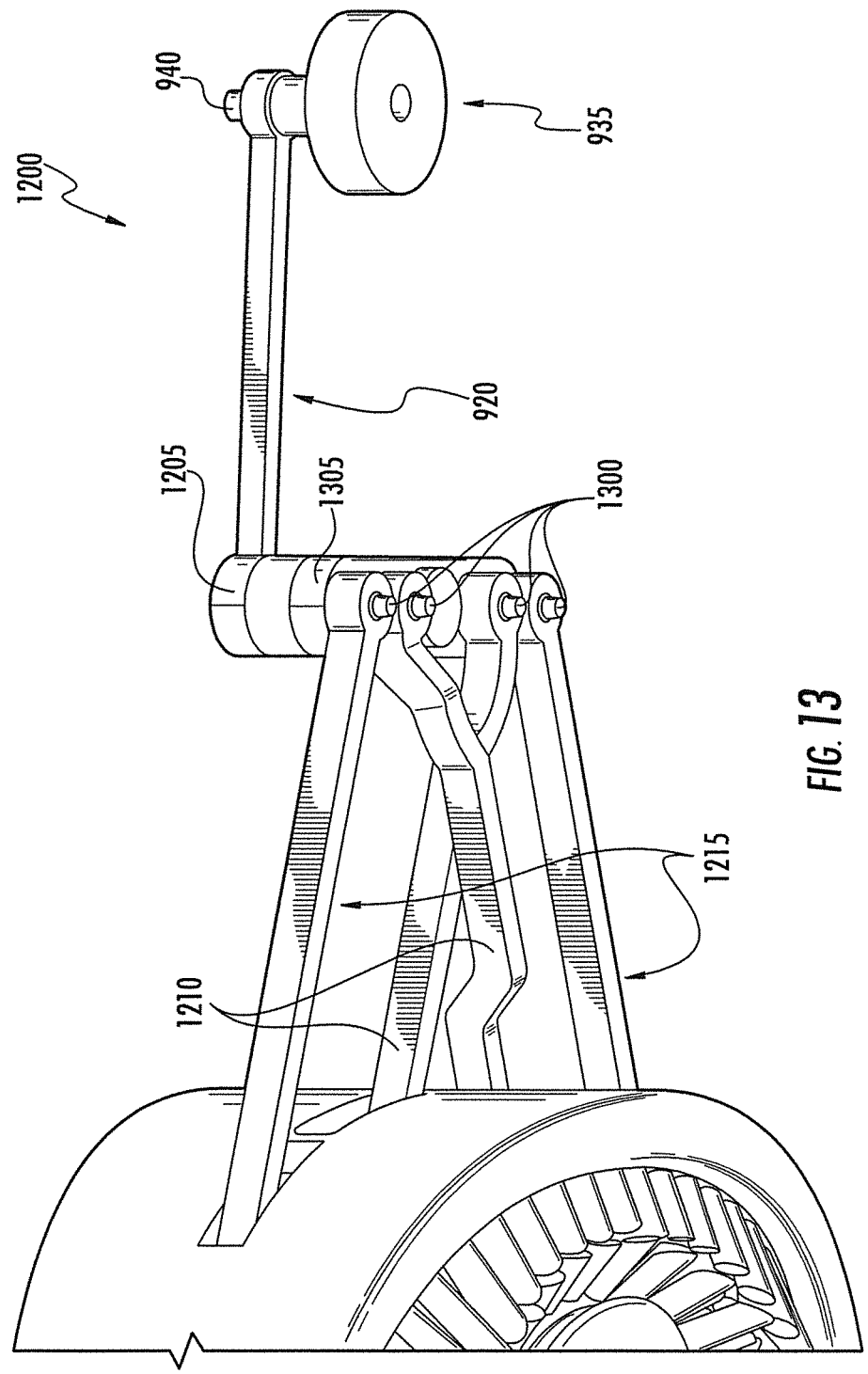
FIG. 13 illustrates an isometric view of an embodiment of the linkage drive assembly of FIG. 12.

With reference to FIGS. 12 and 13, the pivot bar 1205 pivotally communicates with at least one ridged drive linkages 1210, 1215. In one embodiment, the drive linkages 1210, 1215 communicate with wrist pins 1300 on the pivot bar 1205. In another embodiment, the linkages 1210, 1215 each communicate with the pivot bar 1205 utilizing a ball-and-socket joint. The end of each linkage 1210, 1215 not in communication with the pivot bar 1205, engages the bristle strips 500, 510. The linkages 1210, 1215 are made from at least one of high density polyethylene, low density polyethylene, polyethylene terephthalate, polyvinyl chloride, polypropylene, polyoxymethylene, polystyrene, post-consumer resin, K-resin, epoxy resin, phenolic formaldehyde resin, stainless steel, aluminum, ceramic, and any other material known in the art. The pivot bar 1205 is made from made of at least one of high density polyethylene, low density polyethylene, polyethylene terephthalate, polyvinyl chloride, polypropylene, polyoxymethylene, polystyrene, post-consumer resin, K-resin, epoxy resin, phenolic formaldehyde resin, stainless steel, aluminum, ceramic, and any other material known in the art. The linkages 1210, 1215 may include ribs or indentations for strengthening purposes.

FIG. 13 illustrates an example of one embodiment of the drive assembly 500 wherein drive linkages 1210, 1215 pivotally communicate with the pivot bar 1205 by engaging a secondary plate 1305. The linkages are secured to wrist pins 1300. In a preferred embodiment, the wrist pins 1300 capture the pivot bar 1205 with barbed ends. In one embodiment, the center linkages 1210 comprise bends in the lengths of each drive linkage so that the inner drive linkages 1210 can cross paths to avoid mechanical interference.

Figure 14:
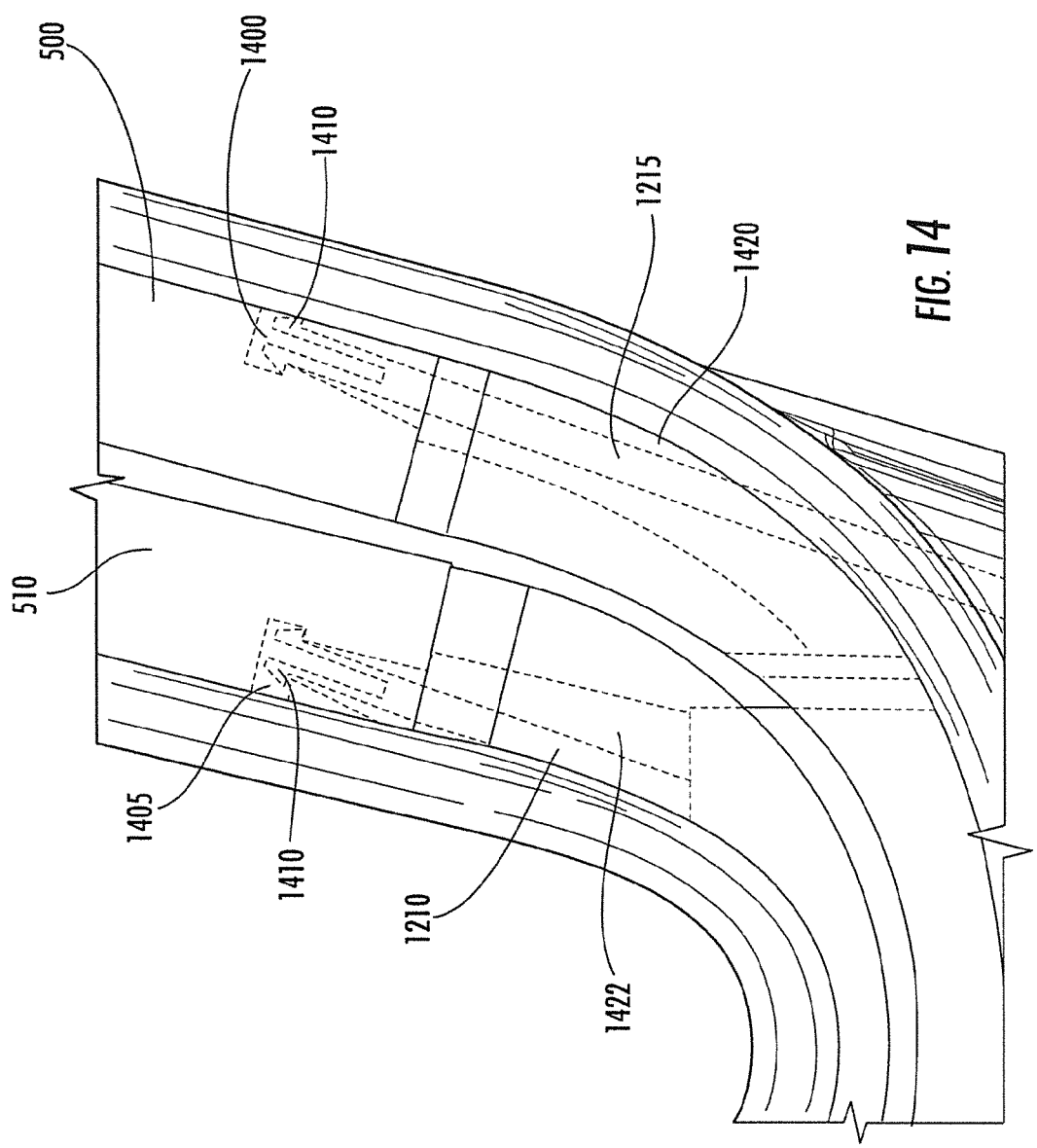
FIG. 14 illustrates a top cutaway view of an embodiment of the linkage drive assembly of FIG. 12.

FIGS. 12, 13 and 14 further illustrate an embodiment of the linkage drive system 900. The drive linkages 1210, 1215 communicate with a bristle strip 500, 510 so to cause the bristle strips 500, 510 to reciprocate. In particular, the outer drive linkage 1215 terminates at opposed attachment points 1400 anchored in the outer bristle strip 500. The inner drive linkage 1210 terminates at opposed attachment points 1405 anchored in the inner bristle strip 510.

With continuing reference to FIG. 14, the outer drive linkage's 1215 two attachment points 1100 alternately reciprocate with the reciprocation of the pivot bar 1205. The inner drive linkage's 1210 two attachment points 1405 alternately reciprocate with the reciprocation of the pivot bar 1205. The attachment points 1400, 1405 each comprise a termination 1410, being at least one of barbs, cuboids, spheres, crimps, tubes, hooks, and loops that are at least one of glued, crimped, tied, molded, and welded to each drive linkage 1210, 1215. The relatively large termination 1410 is trapped in the attachment points 1400, 1405 of a suitable size and dimension to encase the termination 1410, so the termination 1410 is too large to pass through a channel 1420, 1422 in the bristle strip 500, 510, the channel 1120, 1122 however being large enough to accommodate a drive linkage 1210, 1215.

Drive System: Pin Drive

Figure 15:
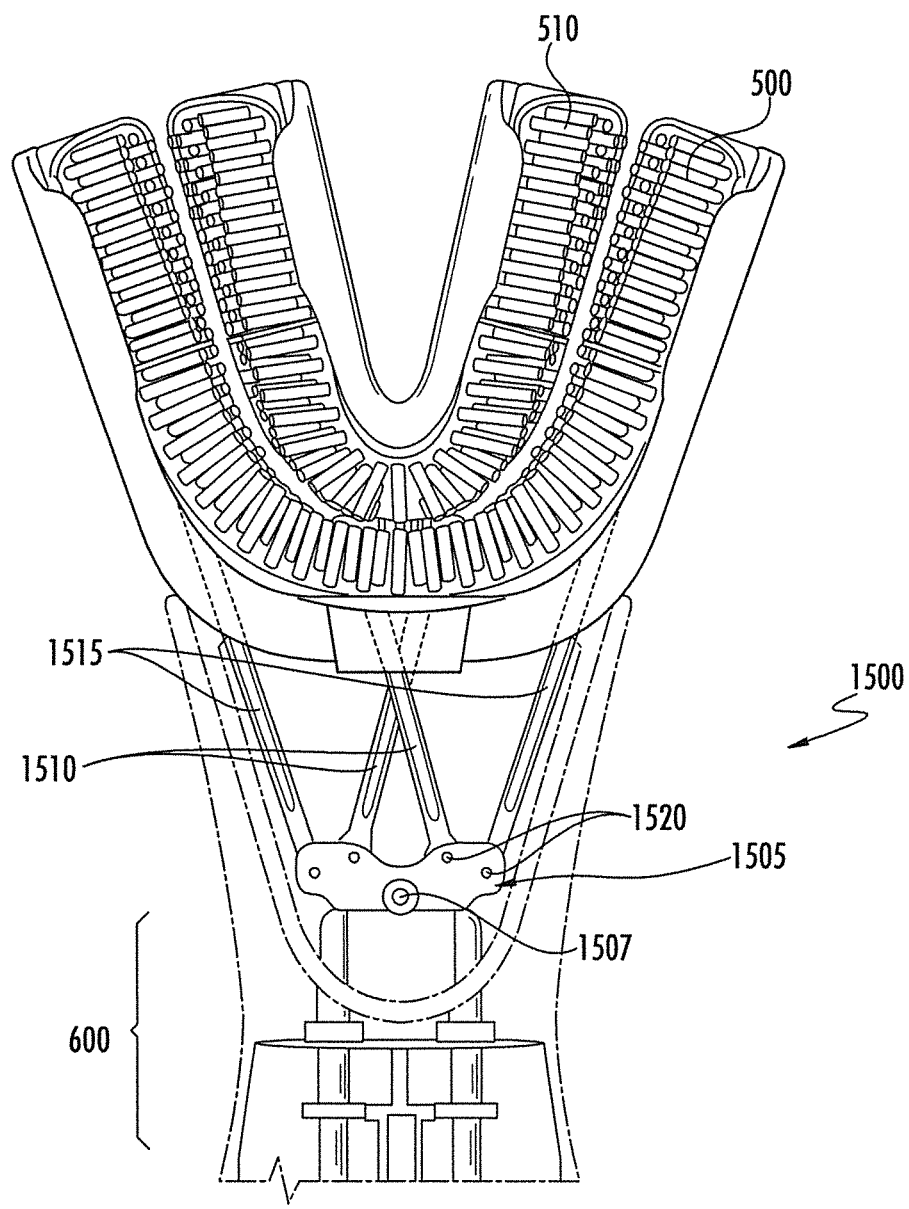
FIG. 15 illustrates a top cutaway view of an embodiment of the pin drive assembly.

FIG. 15 illustrates, by way of example, an alternative embodiment of a pin drive 1500. This embodiment of the drive system is actuated by the reciprocating motion of the first and second reciprocating pins 680, 682 of the gear train 360. The reciprocating pins 680, 682 alternatingly press against a pivot bar 1505, so that the pivot bar 1505 reciprocates on an axle 1507. In this embodiment, the pivot bar 1505 pivotally communicates with at least one ridged drive linkages 1510, 1515. In one embodiment, the drive linkages 1510, 1515 communicate with wrist pins 1520 on the pivot bar 1505. In another embodiment, the drive linkages 1510, 1515 each communicate with the pivot bar 1505 utilizing a ball-and-socket joint. The end of each linkage 1510, 1515 not in communication with the pivot bar 1505, engages the bristle strips 500, 510. The linkages 1510, 1515 are made from at least one of high density polyethylene, low density polyethylene, polyethylene terephthalate, polyvinyl chloride, polypropylene, polyoxymethylene, polystyrene, post-consumer resin, K-resin, epoxy resin, phenolic formaldehyde resin, stainless steel, aluminum, ceramic, and any other material known in the art. The pivot bar 1505 is made from made of at least one of high density polyethylene, low density polyethylene, polyethylene terephthalate, polyvinyl chloride, polypropylene, polyoxymethylene, polystyrene, post-consumer resin, K-resin, epoxy resin, phenolic formaldehyde resin, stainless steel, aluminum, ceramic, and any other material known in the art. The linkages 1210, 1215 may include ribs or indentations for strengthening purposes.

Figure 16:
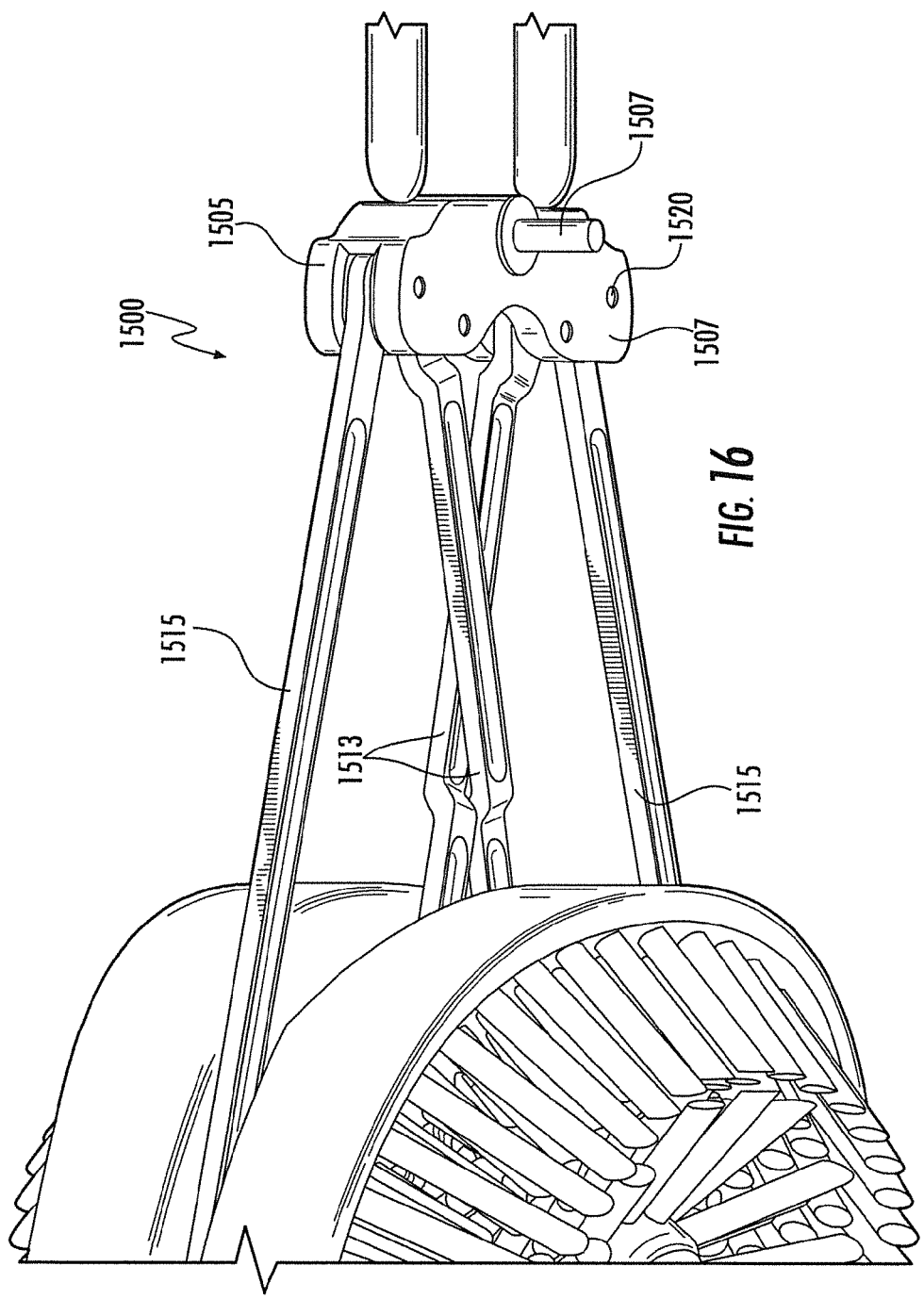
FIG. 16 illustrates an isometric view of an embodiment of the pin drive assembly of FIG. 15.

FIG. 16 illustrates an example of one embodiment of the pin drive assembly 1500 wherein drive linkages 1510, 1515 pivotally communicate with the pivot bar 1505 by engaging a secondary plate 1507. The drive linkages 1510, 1515 are secured to wrist pins 1520. In one embodiment, the inner drive linkages 1510 comprise bends in the lengths of each drive linkage so that the inner drive linkages 1510 can cross paths to avoid mechanical interference.

Figure 17:
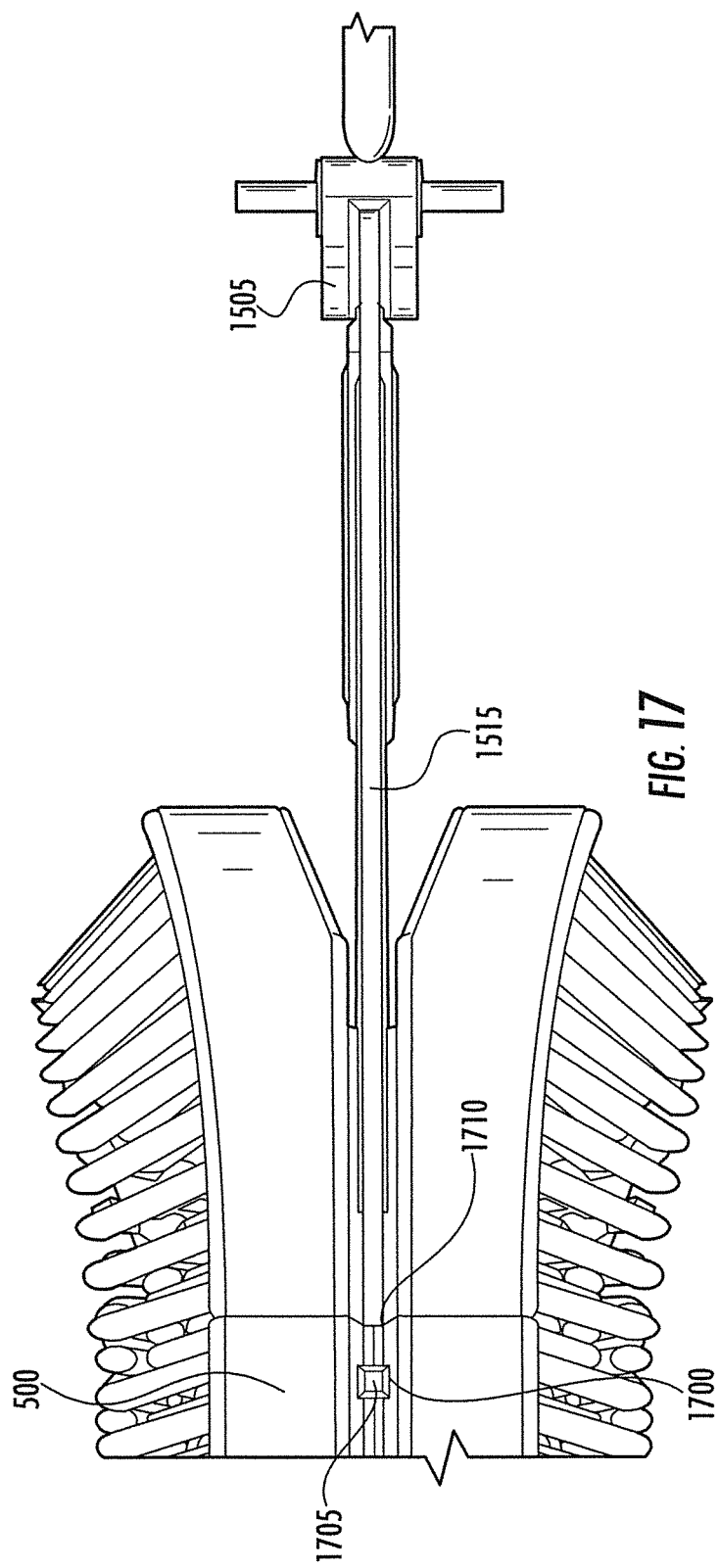
FIG. 17 illustrates a side cutaway view of an embodiment of the pin drive assembly of FIG. 15.

FIGS. 15, 16 and 17 further illustrate an embodiment of the linkage drive system 1500. The drive linkages 1510, 1515 each communicate with a bristle strip 500, 510 so to cause the bristle strips 500, 510 to reciprocate. In particular, the outer drive linkage 1515 terminates at opposed attachment points 1700 anchored in the outer bristle strip 500. The inner drive linkage 1510 terminates at opposed attachment points (not shown) anchored in the inner bristle strip 510.

With continuing reference to FIGS. 15, 16, and 17 the outer drive linkage's 1515 two attachment points 1700 alternately reciprocate with the reciprocation of the pivot bar 1505. The inner drive linkage's 1510 two attachment points alternately reciprocate with the reciprocation of the pivot bar 1505. The attachment points 1700 each comprise a termination 1705, being at least one of barbs, cuboids, spheres, crimps, tubes, hooks, and loops that are at least one of glued, crimped, molded, tied, and welded to each drive linkage 1510, 1515. The relatively large termination 1705 is trapped in the attachment points 1700 of a suitable size and dimension to encase the termination 1705, so each termination 1705 is too large to pass through a channel 1710 in each bristle strip 500, 510, the channel 1710 however being large enough to accommodate a drive linkage 1510, 1515.

Bristle Strips

Figure 18:
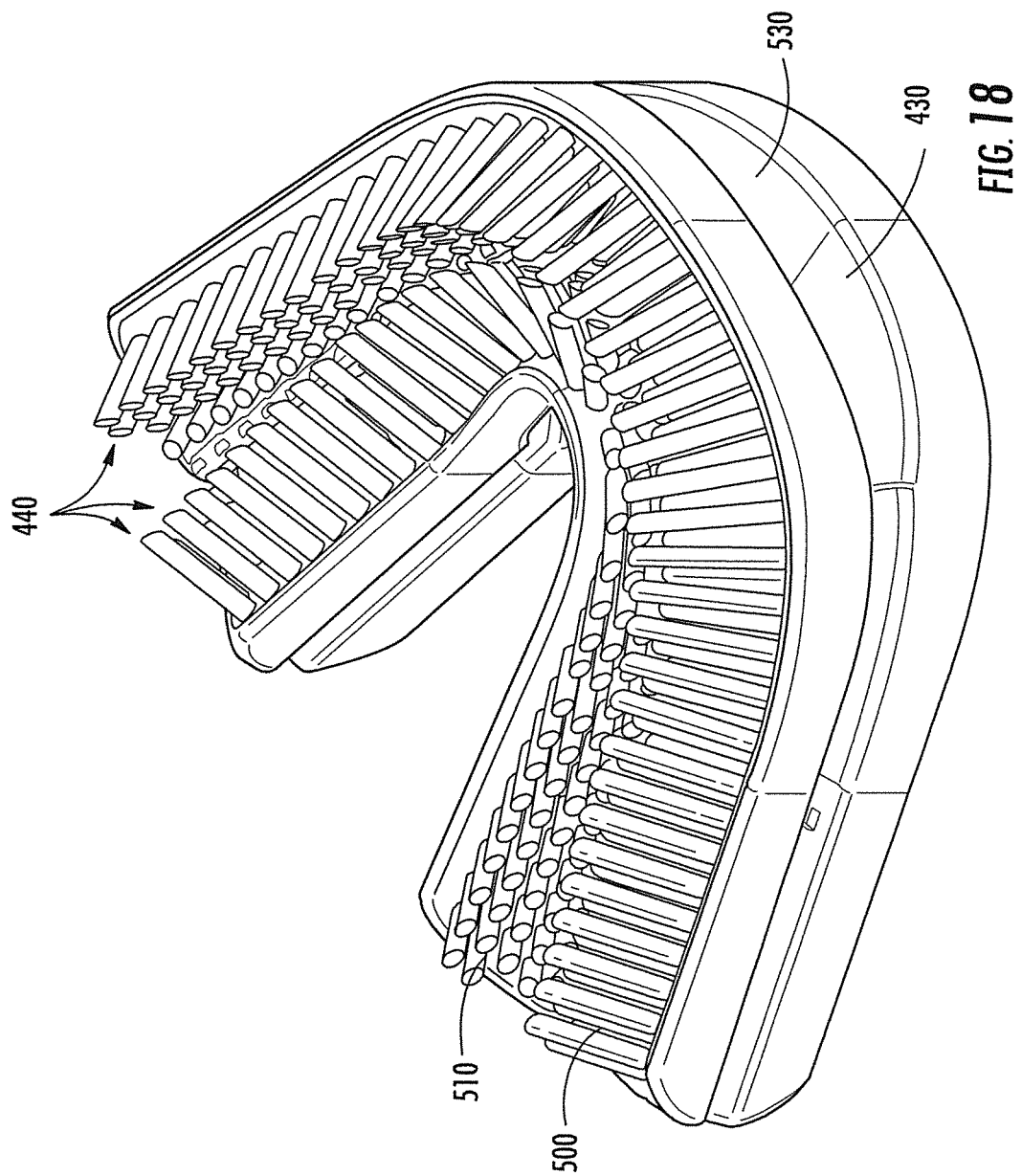
FIG. 18 illustrates an isometric view of an embodiment of inner and outer bristle strips.

FIG. 18 illustrates an embodiment of inner and outer bristle strips 500, 510. Also described above and illustrated in FIGS. 4 and 5, the bristle strips 500, 510 comprise a plurality of bristle bundles 440, and engage the inner and outer frames 430, 410 of the mouthpiece assembly 400. The bristle strips 500, 510, are of a flexible or hinged type.

The bristles bundles 440 of the inner bristle strip 510 engage both the upper and lower lingual, occlusal, and incisal teeth surfaces. The bristle bundles 440 of the outer bristle strip 500 engage both the upper and lower facial, occlusal, and incisal teeth surfaces. In combination, the bristle bundles 440 of the bristle strips 500, 510 are designed to engage and clean all teeth surfaces simultaneously. Different sizes and shapes of the bristle strips 500, 510 are contemplated to accommodate a variety of mouth shapes and sizes.

The bristle strips 500, 510 embodiments herein described comprise a plurality of bristle bundles 440. The individual bristles of these bundles 440 are made from at least one of plastic, nylon, natural fibers (such as boar's hair or bamboo), thin metal (such as titanium), and any other material known in the art. In one embodiment, the bristles are substantially evenly distributed on the bristle bearing surfaces of the bristle strips 500, 510. In another embodiment, the bristles are organized into bristle bundles 440 of approximately 10 to 100 individual bristles. Bristle bundles 440 are available in a plurality of configurations. In one embodiment, bristle bundles 440 are organized with bristles of varying lengths to form a pointed bristle bundle 440 (The longer bristles being in the center of the bundle 440, progressively getting shorter as the radius of the bristle bundle 440 increases). In another embodiment, the bristle bundle 440 is organized with bristles of varying lengths to form a cupped bristle bundle 440 (The shorter bristles being in the center of the bundle 440, progressively getting longer as the radius of the bristle bundle 440 increases). Other variations include a chiseled bristle bundle 440 profile, and a flat bristle bundle 440 profile. In one embodiment, differing bristle bundle configurations are distributed amongst different regions of the bristle strips 500, 510. Longer bristle bundles 440 are typically for the cleaning of the facial or lingual faces of teeth as well as the gum line. Shorter bristle bundles 440 typically clean the occlusal and incisal surfaces of teeth. Bristles are approximately perpendicular to the bristle strip, but the bristle strip itself comprises a multitude of contoured surfaces to allow the bristles to be angled in relation to the teeth. In one embodiment, bristles shorten towards the molar-contacting end of the bristle strip to accommodate greater molar width.

Bristle Strips: Flexible

Figure 19:
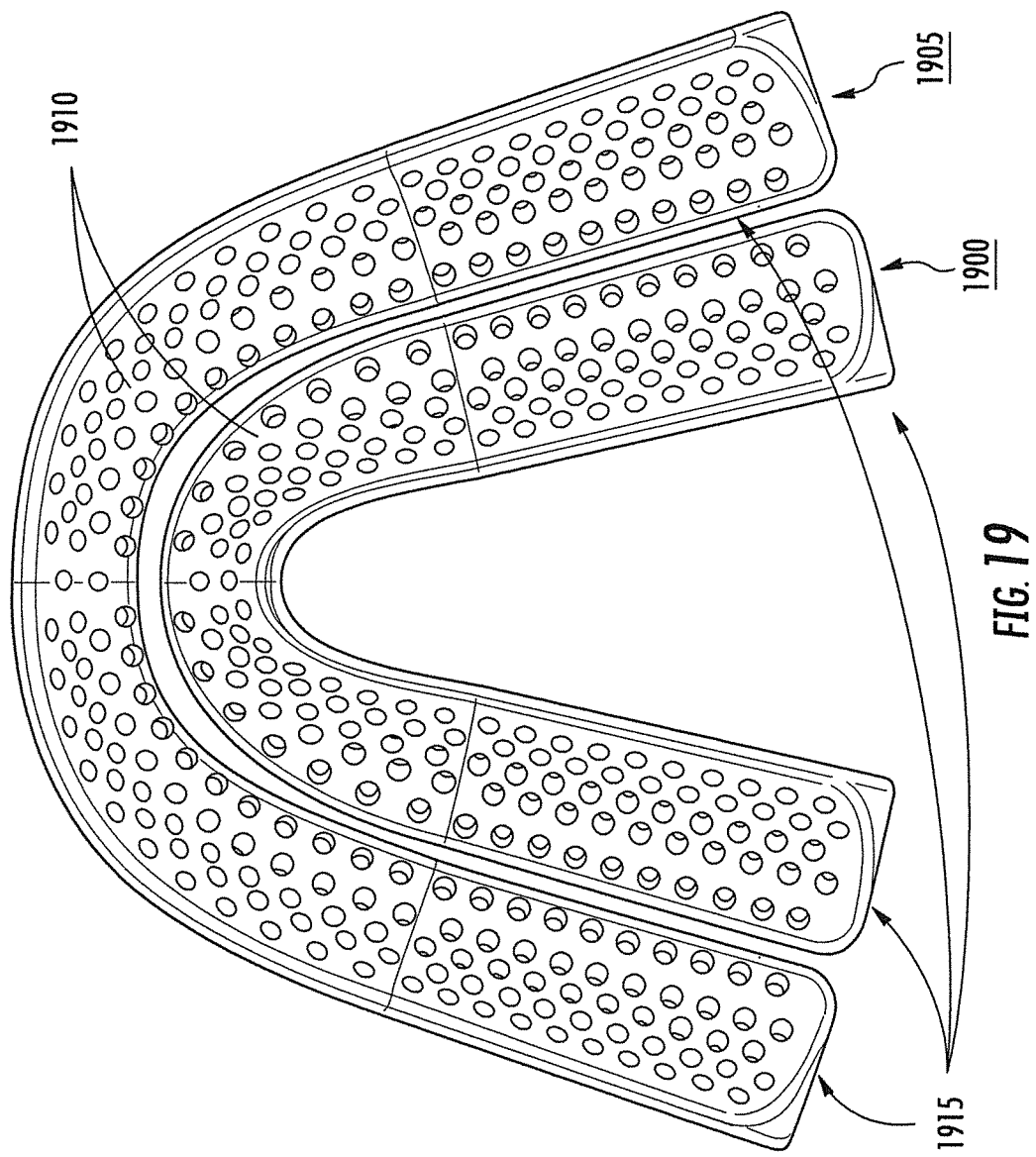
FIG. 19 illustrates a top view of the embodiment of inner and outer bristle strips of FIG. 18 without any bristle bundles for clarity.
Figure 20:
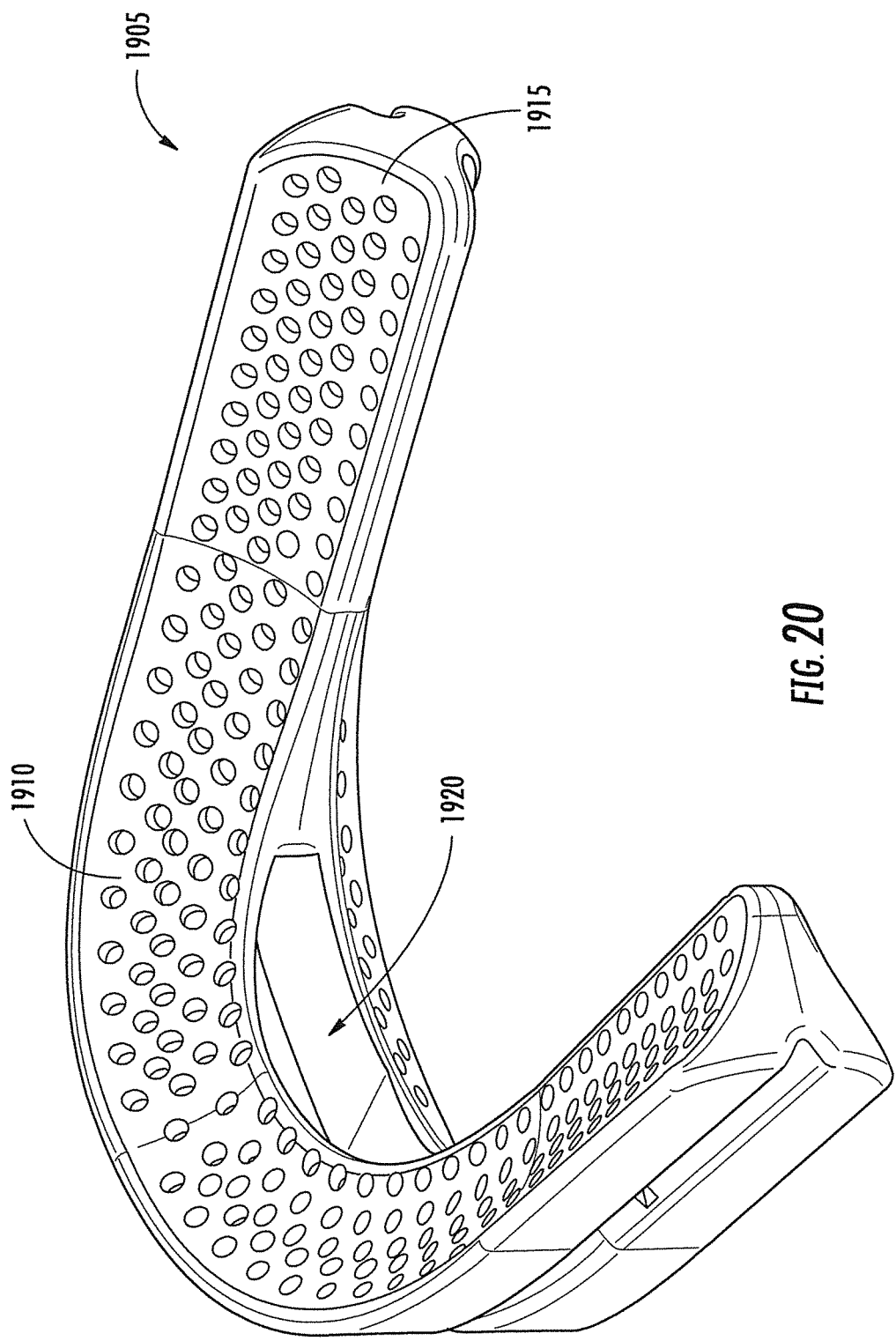
FIG. 20 illustrates an isometric view of the embodiment of an outer bristle strip of FIG. 18 without any bristle bundles for clarity.

FIGS. 19 and 20 illustrate an inner flexible bristle strip 1900 and an outer flexible bristle strip 1905. The bristle bundles 440 are not shown for the sake of clarity. The flexible bristle strips 1900, 1905 each have a middle flexible region 1910 and rigid end sections 1915. In another embodiment, the bristle strips 1900, 1905 are substantially the same durometer throughout. The middle flexible regions 1910 communicate with approximately the incisor/cuspid/premolar regions of a user's mouth, and the rigid end sections 1915 communicate with the approximately the premolar/molar regions of a user's mouth. FIG. 20 illustrates an aperture 1920 in the middle flexible region 1920 of the outer bristle strip 1905 for the purpose of allowing drive wires 910, 915 or linkages 1210, 1215, 1510, 1515 and inner 430 and outer frame 410 portions to pass.

Bristle Strips: Hinged

Figure 21:
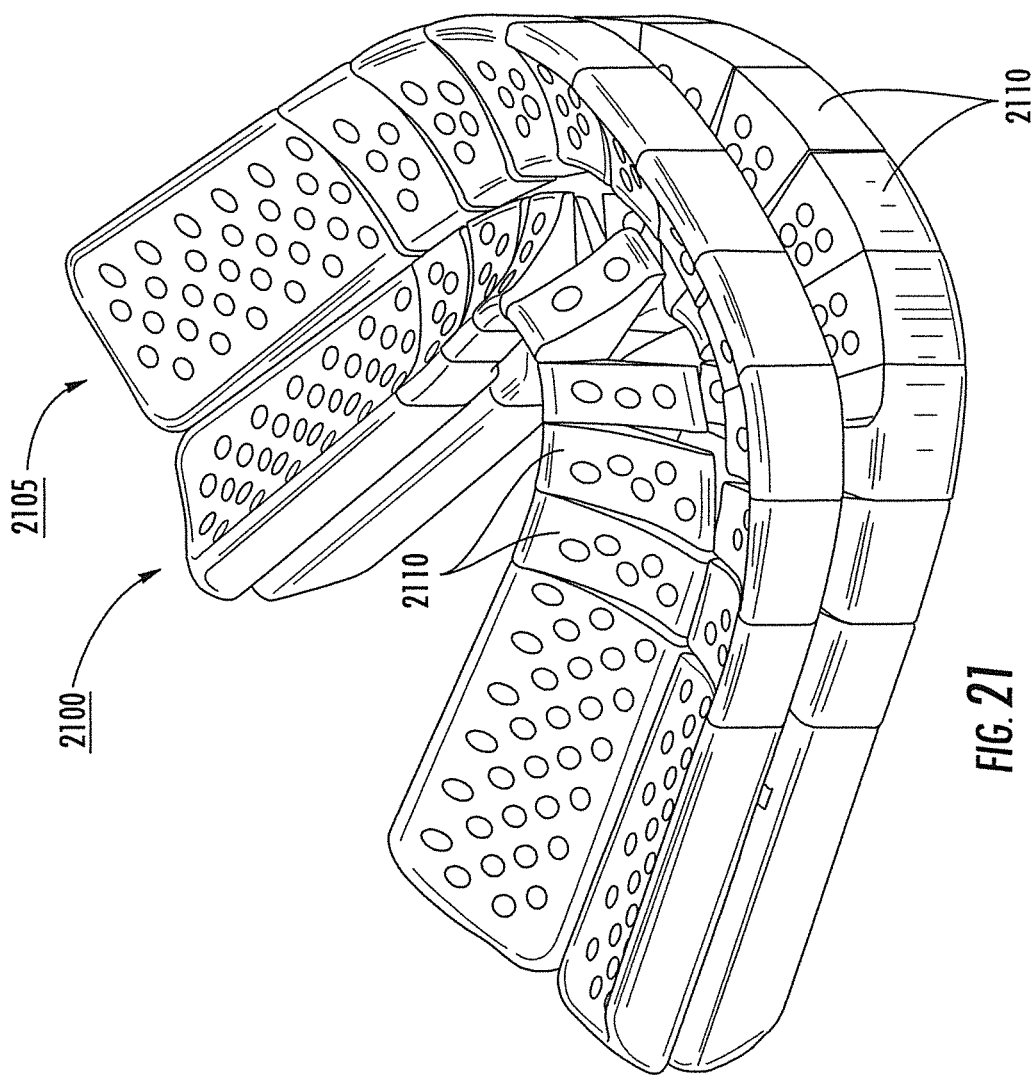
FIG. 21 illustrates an isometric view of an embodiment of a hinged inner and outer bristle strips without any bristle bundles for clarity.
Figure 22:
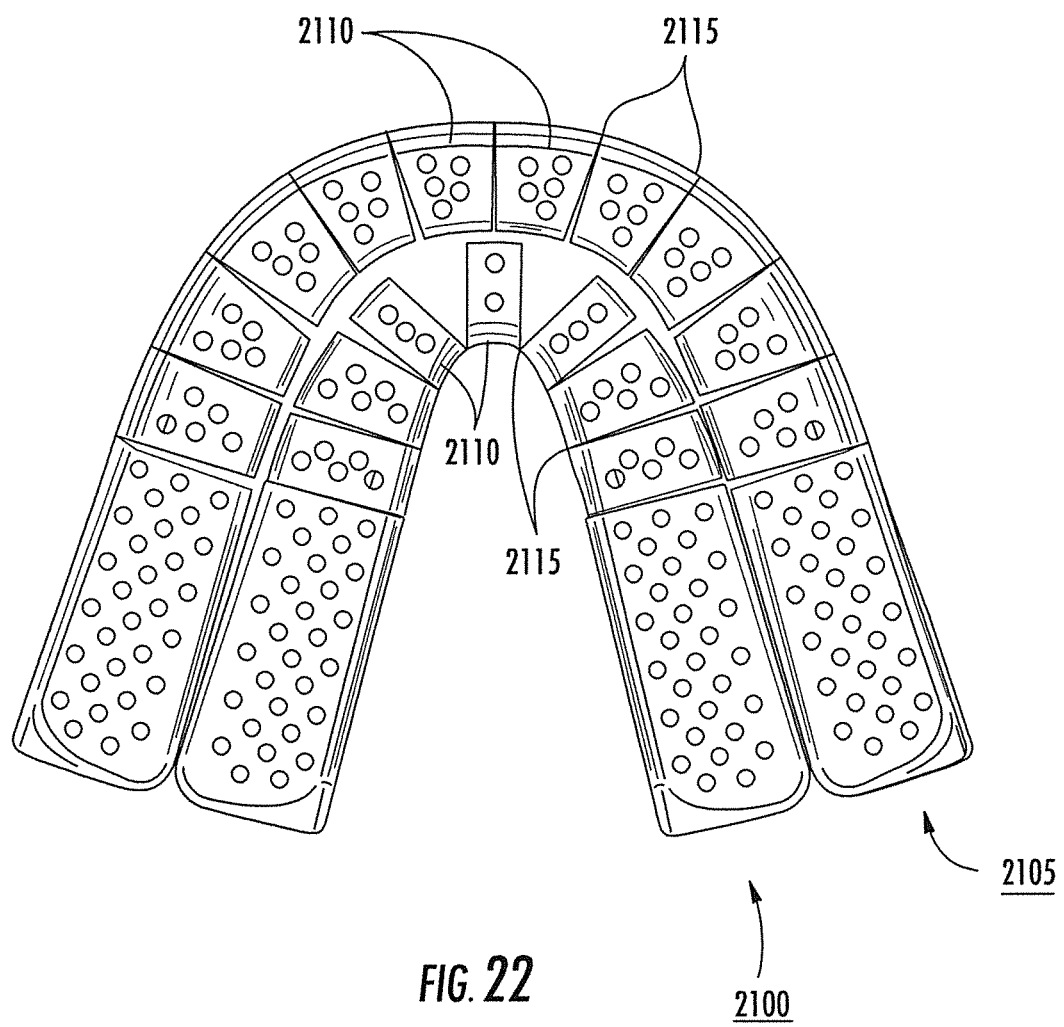
FIG. 22 illustrates a top view of an embodiment of the hinged inner and outer bristle strips of FIG. 21 without any bristle bundles for clarity.

FIGS. 21 and 22 illustrate, by way of example, one embodiment of a hinged inner bristle strip 2100 and a hinged outer bristle strip 2105. The bristle strips 2100, 2105 comprise a plurality of segments 2110, each segment 2110 capable of engaging a plurality of bristle bundles 440. The segments 2110 are hingedly linked to each other at individual hinges 2115. In one embodiment, exemplified by the illustrations of FIG. 21 and FIG. 22 the bristle strips 2100, 2150 are of a unibody construction with a series of linked segments 2110 that each hingedly communicates with adjacent linked regions 2110 through living hinges.

Figure 23:
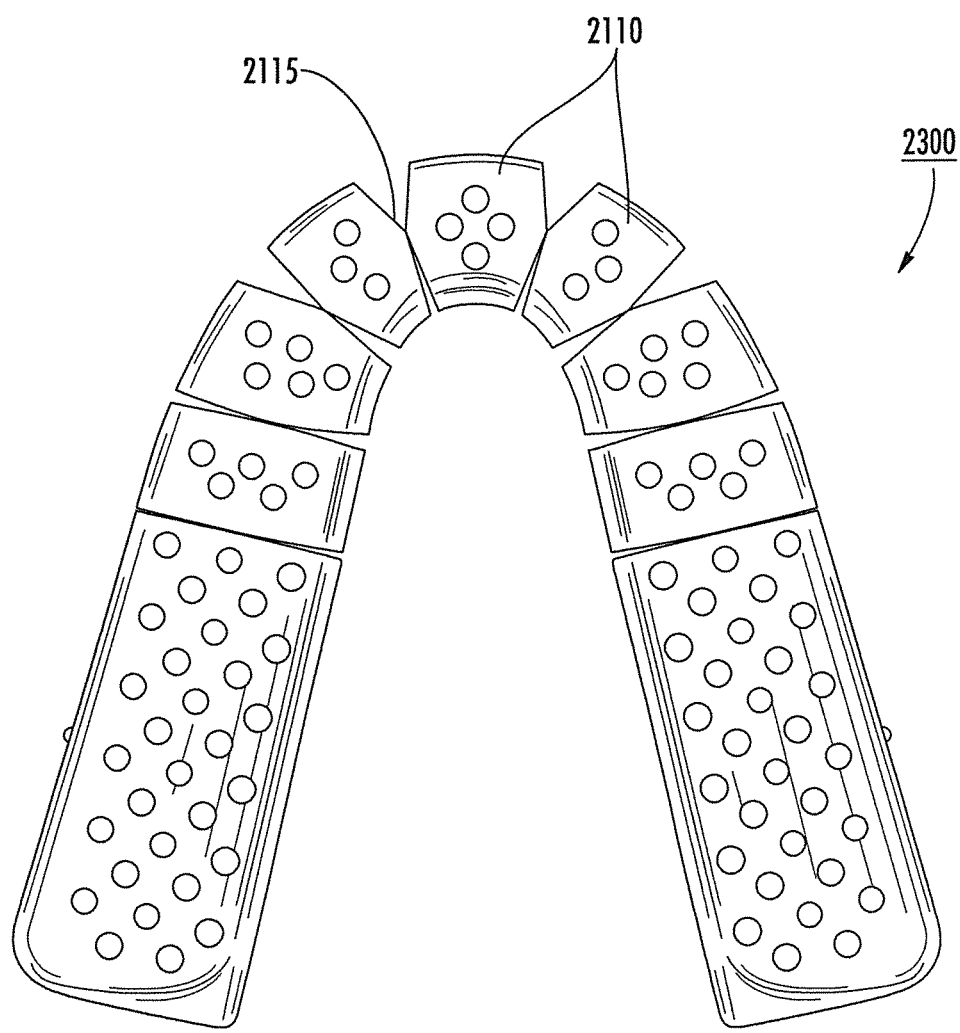
FIG. 23 illustrates a top view of an embodiment of a hinged inner bristle strip without any bristle bundles for clarity.
Figure 24:
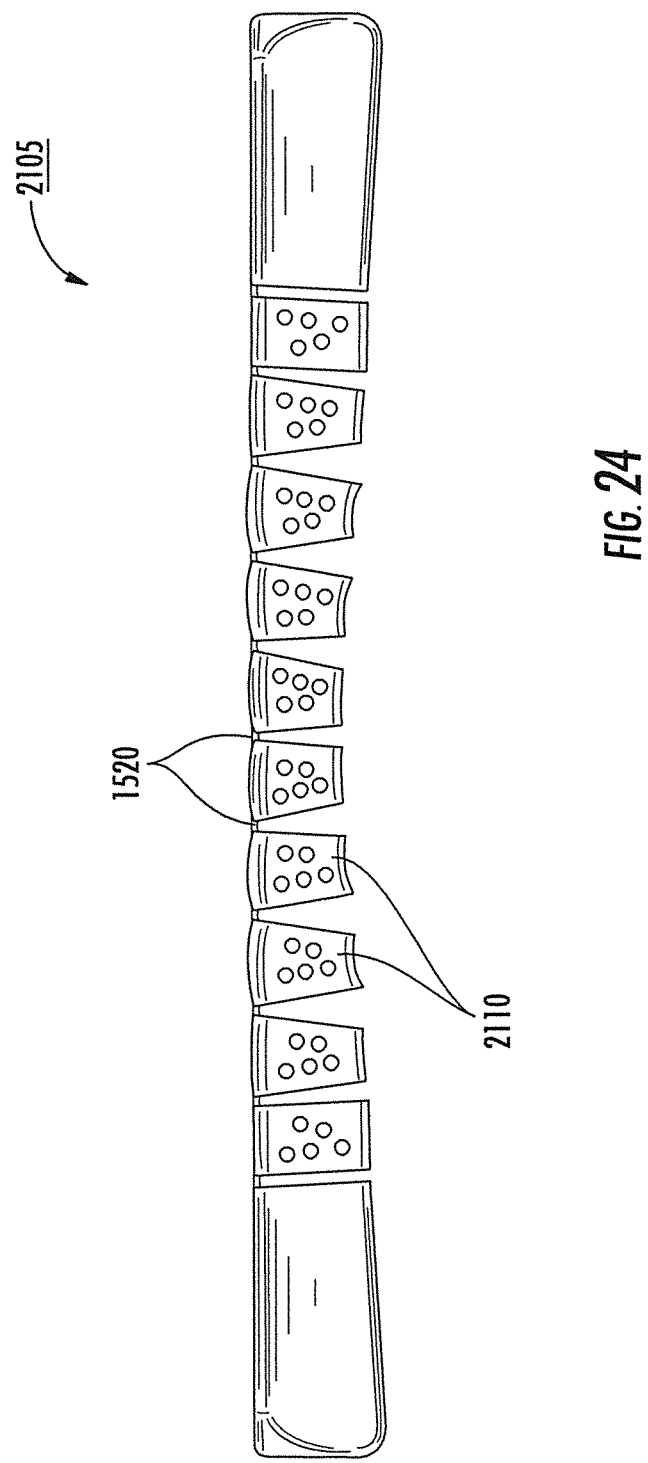
FIG. 24 illustrates a top view of an embodiment of a hinged outer bristle strip without any bristle bundles for clarity and in an extended conformation.

In the embodiment illustrated in FIG. 22, the hinges 2115 are situated at an edge of the bristle strips 2100, 2105. The edge can be either the inner edge as shown on the inner bristle strip 2100, or the outer edge as shown on the outer bristle strip 2105. The embodiment of FIG. 23 illustrates the hinges 2115 situated in the middle of the segments 2110. Though these illustrations show middle or edge hinges 2115 on a particular bristle strip (either inner or outer) these hinge placements are equally applicable to the alternative bristle strip not specifically exemplified.

As illustrated in FIGS. 21-24, the segments 2110 are each shaped to allow the necessary degree of hinged flexibility between the hinges 2115 so that the bristle strips 2100, 2105 can form a substantially semi-elliptical conformation.

In one embodiment, the bristle strips 2100, 2105 comprise regions of differing durometer. The segments 2110 of the bristle strips 2100, 2105 that communicate substantially with the incisor, cuspid, and premolar teeth are comprised of a flexible material, while the region of the bristle strips 2100, 2105 that communicate substantially with the molars are approximately rigid. In another embodiment, the bristle strips 2100, 2105 are substantially the same durometer throughout.

Figure 25:
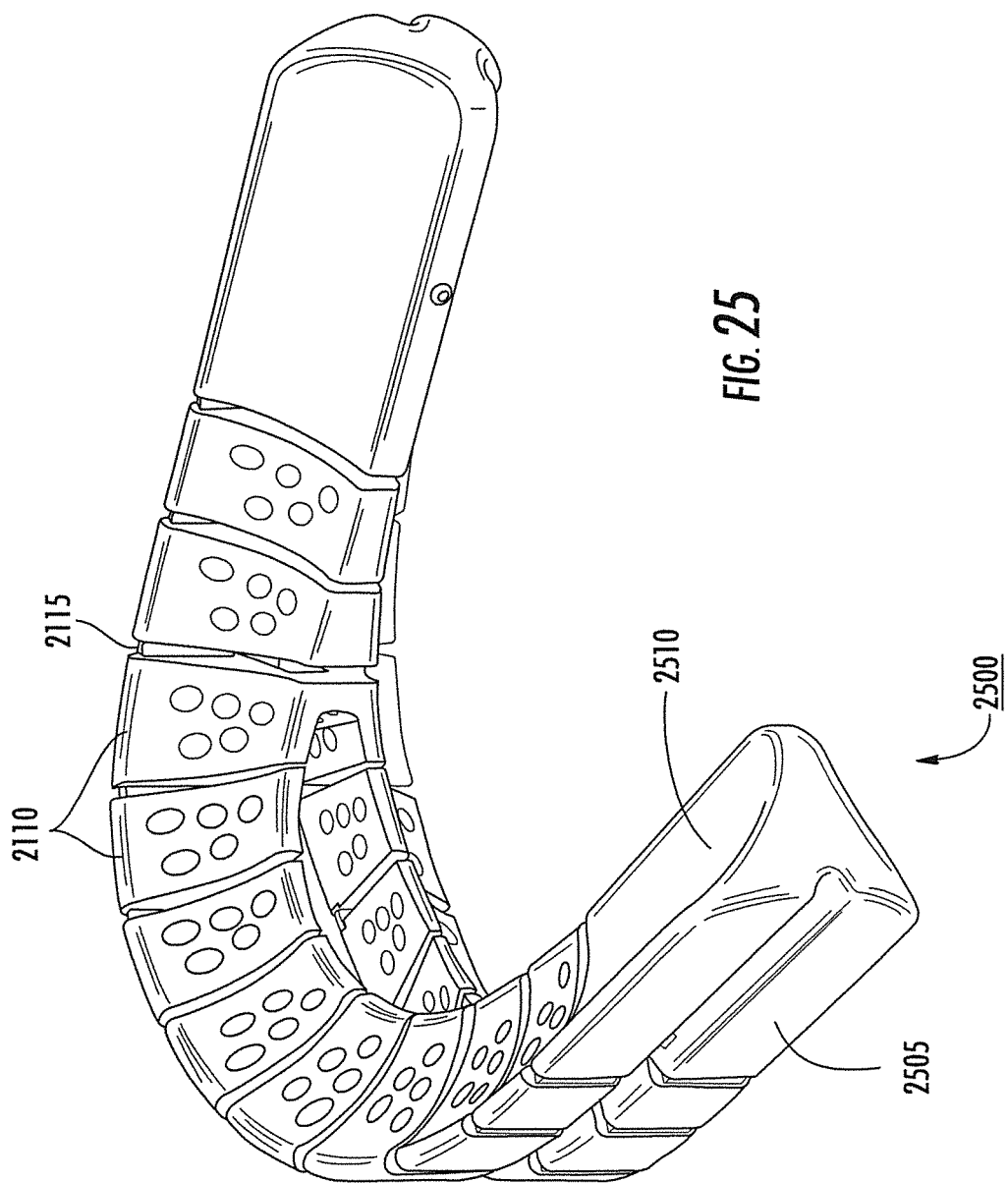
FIG. 25 illustrates an isometric view of an embodiment of an overmolded outer bristle strip without any bristle bundles for clarity.

FIG. 25 illustrates that instead of living hinges as hinges 2115 between segments 2110, as illustrated in FIG. 25, the hinges 2115 in an alternate embodiment are constructed from overmolding. In this case, an overmolded layer 2505 is bonded to a base material 2510, together forming the bristle strip 2500. The overmolding 2505 is a flexible material so that the segments 2110 can hingedly move to allow the bristle strip 2500 to form substantially a U shape.

Figure 26:
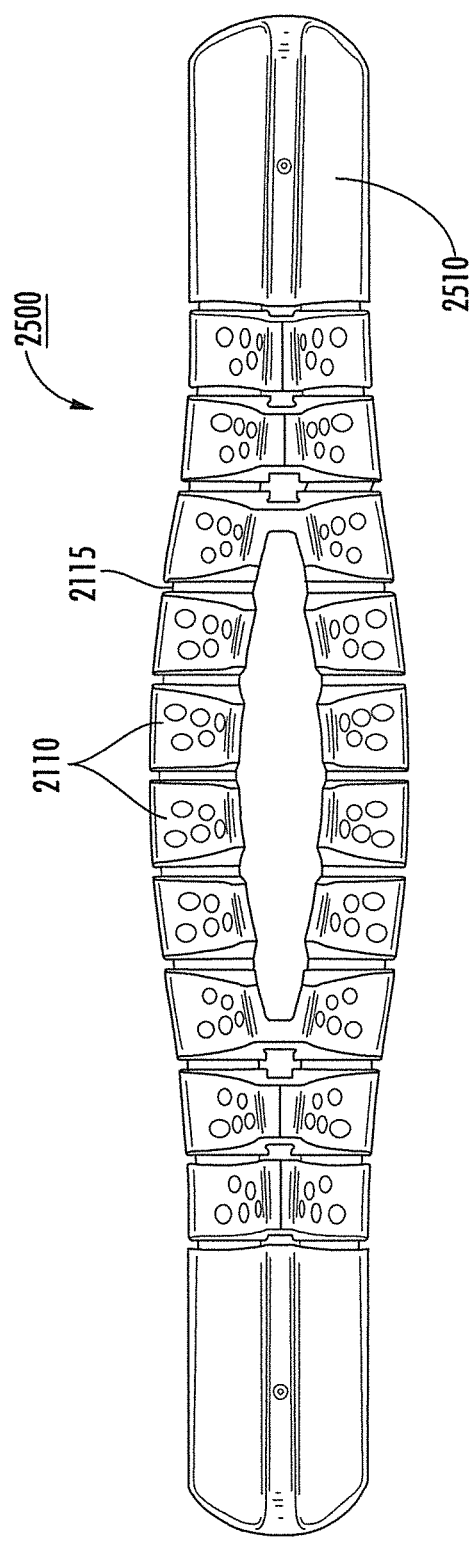
FIG. 26 illustrates a side view of an embodiment of the overmolded outer bristle strip of FIG. 25 without any bristle bundles for clarity and in an extended conformation.

FIG. 26 illustrates the overmolded bristle strip 2500 in a flat conformation. Due to the flexibility conferred upon the bristle strip 2500 due to the overmolded layer 2505, the bristle strip 2500 can be flattened for manufacturing or assembly. The overmolding 2505 runs substantially the entirety of the thickness of edge of the segments 2110. In an alternative embodiment, the overmolding 2505 runs only a portion of the length of the thickness of edge of the segments 2110.

Non-Framed Rigid Beam Mouthpieces

Figure 27:
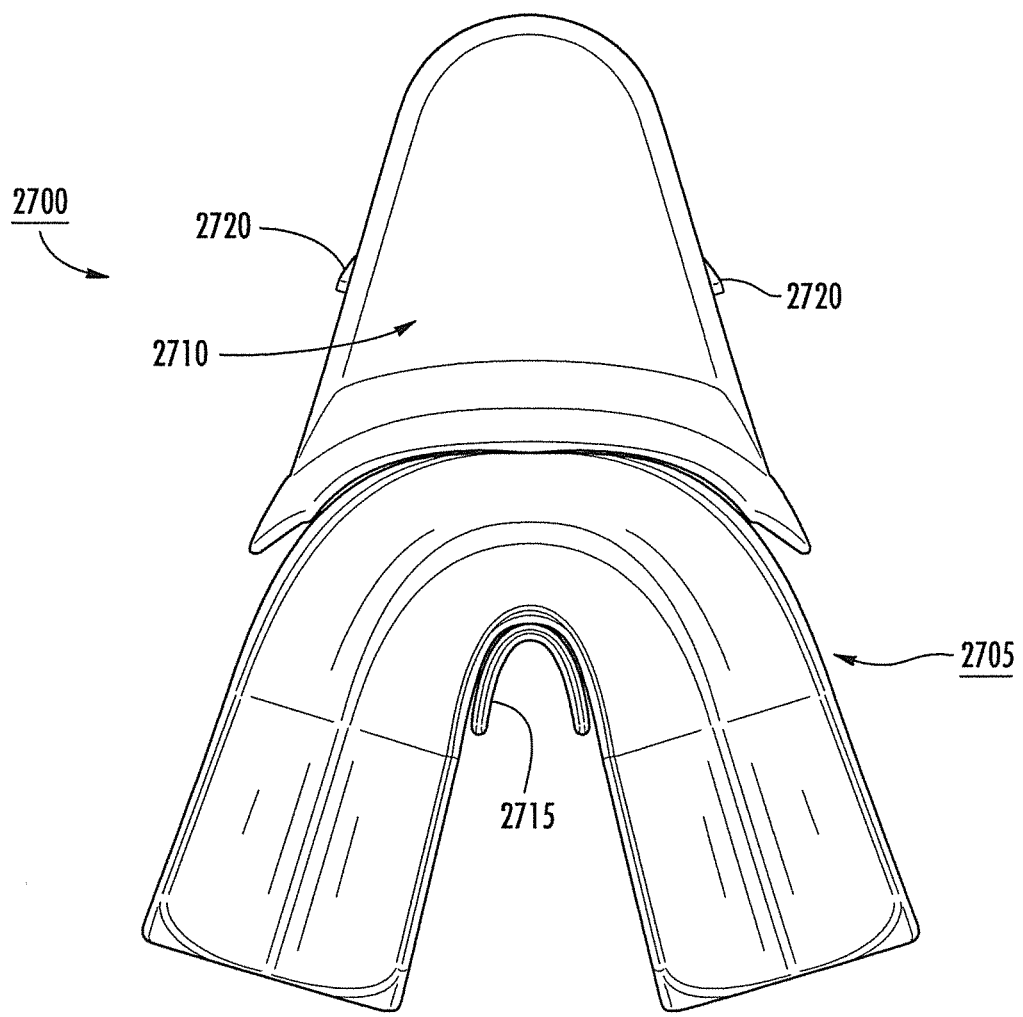
FIG. 27 illustrates a top view of an embodiment of a non-framed rigid beam mouthpiece without any bristle bundles for clarity.
Figure 28:
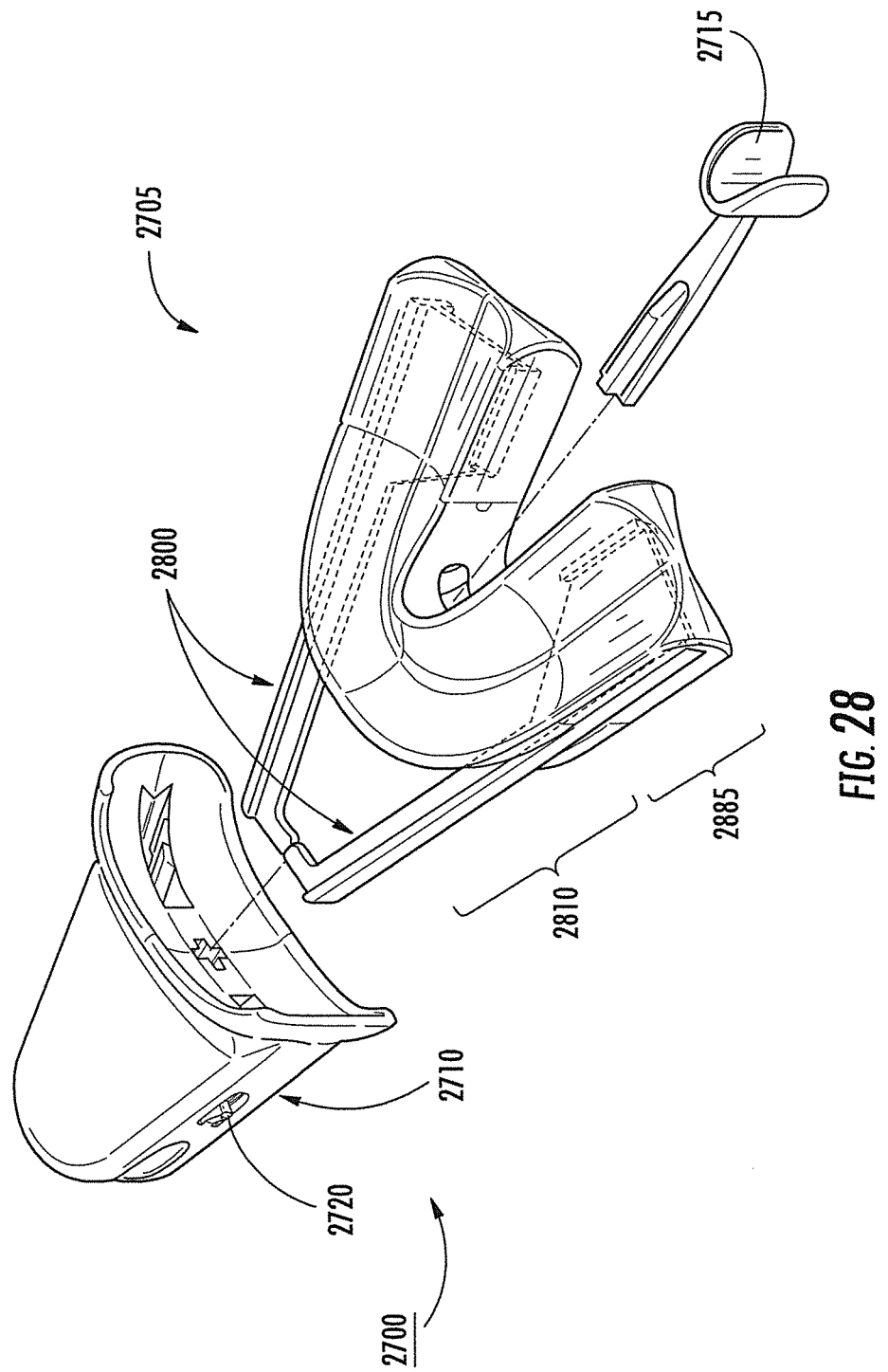
FIG. 28 illustrates an exploded isometric view of an embodiment of the non-framed rigid beam mouthpiece of FIG. 27 without any bristle bundles for clarity.

FIGS. 27-30 illustrate an embodiment of a non-framed rigid beam mouthpiece 2700. As illustrated in FIG. 27, a bristle strip assembly 2705 engages an outer guard 2710, and is secured in place by an inner guard 2715 that engages the outer guard 2710 through the bristle strip assembly 2705. In one embodiment, the inner guard 2715 is welded to the outer guard 2710. The outer guard 2710 comprises snap hooks 2720 for securing the mouthpiece to a handle 210. FIG. 28 also illustrates the assembly described above and illustrated in FIG. 27.

Figure 29:
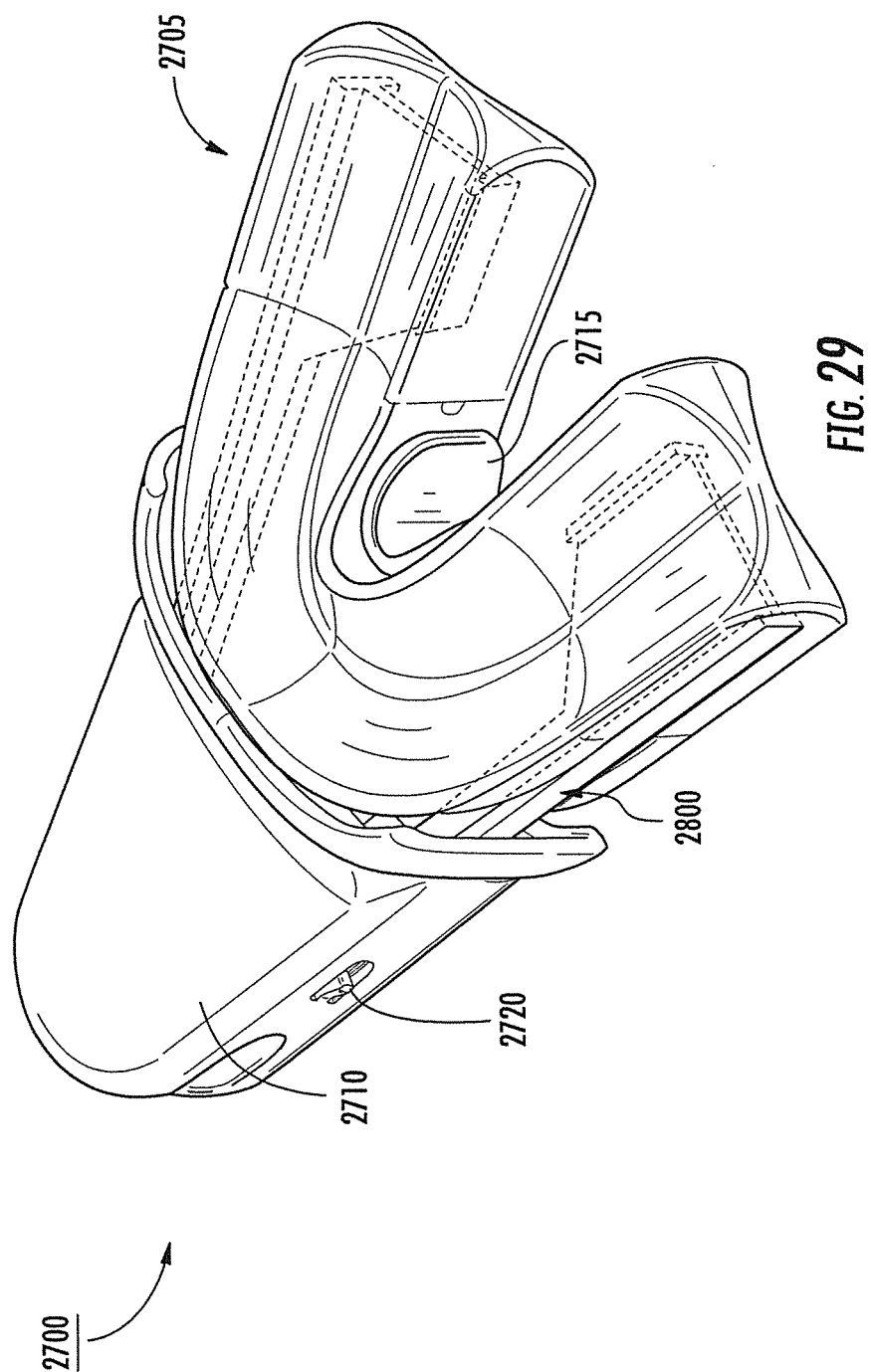
FIG. 29 illustrates an isometric view of an embodiment of the non-framed rigid beam mouthpiece of FIG. 27 without any bristle bundles for clarity.
Figure 30:
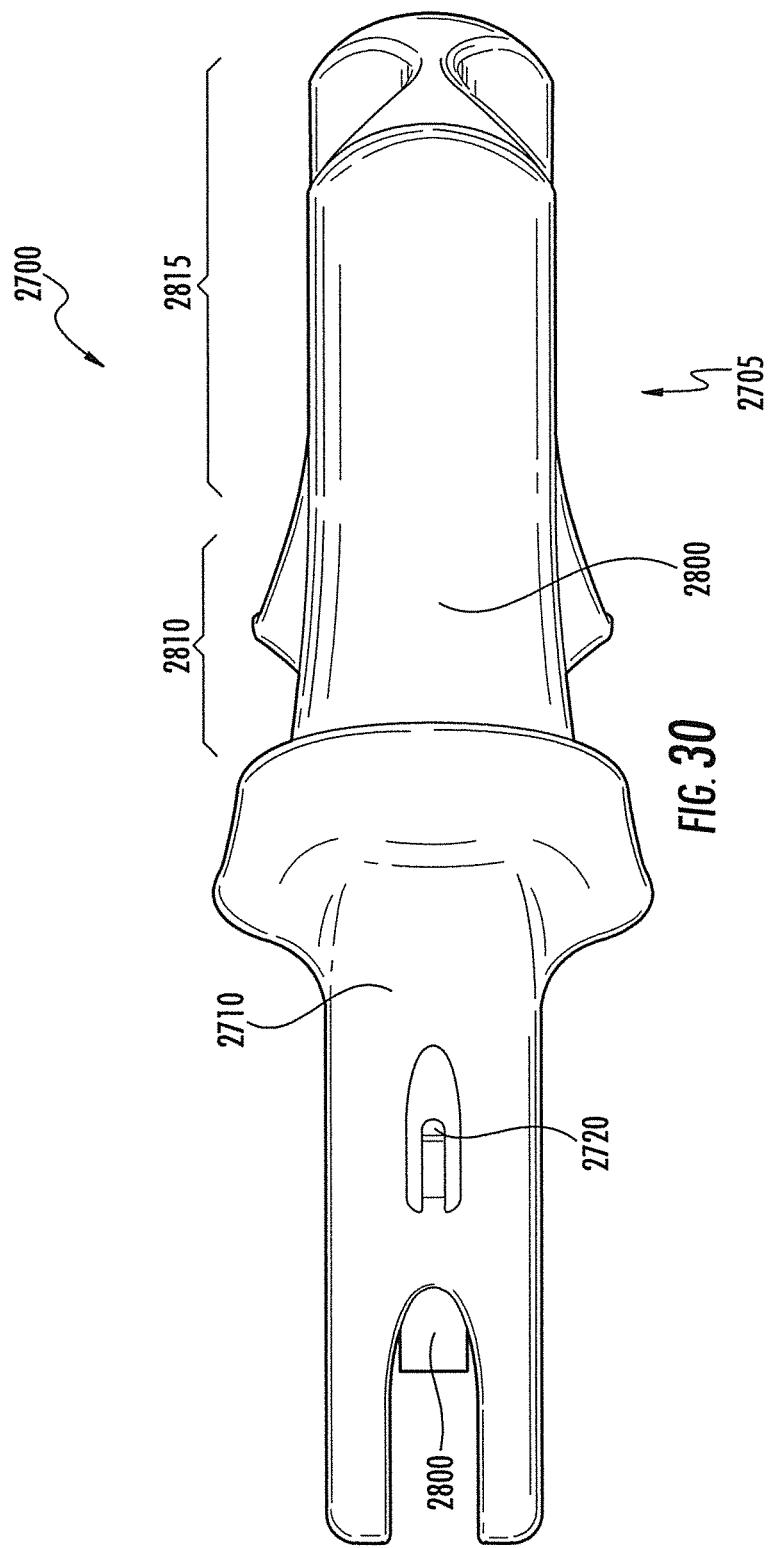
FIG. 30 illustrates a side view of an embodiment of the non-framed rigid beam mouthpiece of FIG. 27 without any bristle bundles for clarity.

FIGS. 28 and 29 illustrate, among other things, the rigid beams 2800 of the bristle strip assembly 2705. The rigid beams 2800 promote structural integrity of the bristle strip assembly 2705. They also provide the means for the bristle strips to communicate with the gear train 700 so that the reciprocating motion of the reciprocating pins 780, 782 is conferred to the bristle strips.

The rigid beams 2800 are made of at least one of high density polyethylene, low density polyethylene, polyethylene terephthalate, polyvinyl chloride, polypropylene, polyoxymethylene, polystyrene, post-consumer resin, K-resin, epoxy resin, phenolic formaldehyde resin, stainless steel, aluminum, ceramic, and any other material known in the art. In a preferred embodiment, the rigid beams 2800 are made from a substantially non-reactive substance such as stainless steel.

The bristle strip assembly 2705 can comprise regions of varying durometer. The flexible region 2810 that communicates substantially with the incisor, cuspid, and premolar teeth is comprised of a flexible material, while the rigid regions 2885 of the bristle strip assembly 2705 that communicate substantially with the molars are approximately rigid. The flexible region 2810 allows the bristle strip to move around the curve of the dental arch due to the flexible region's 2810 compliance.

Rigid Beam Mouthpiece: H-Beam

Figure 31A:
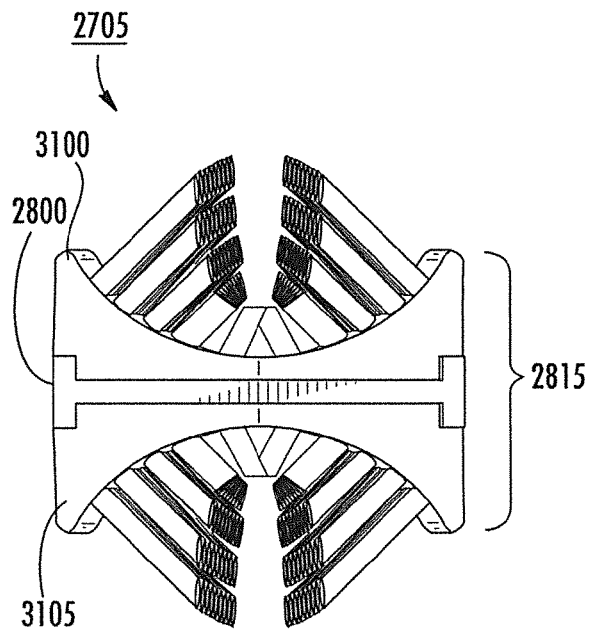
FIG. 31a illustrates a cross-sectional view of a bristle strip used in the mouthpiece of FIG. 27.
Figure 31B:
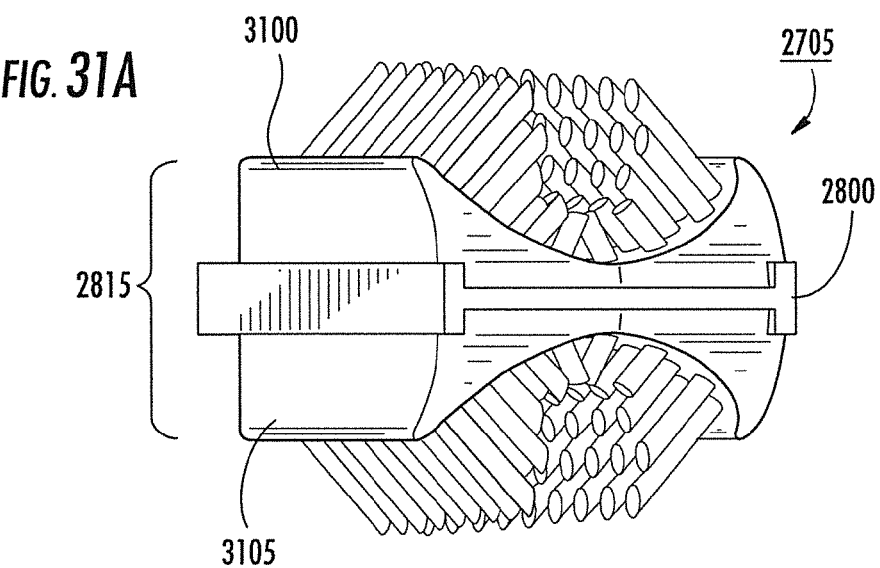
Figure 32:
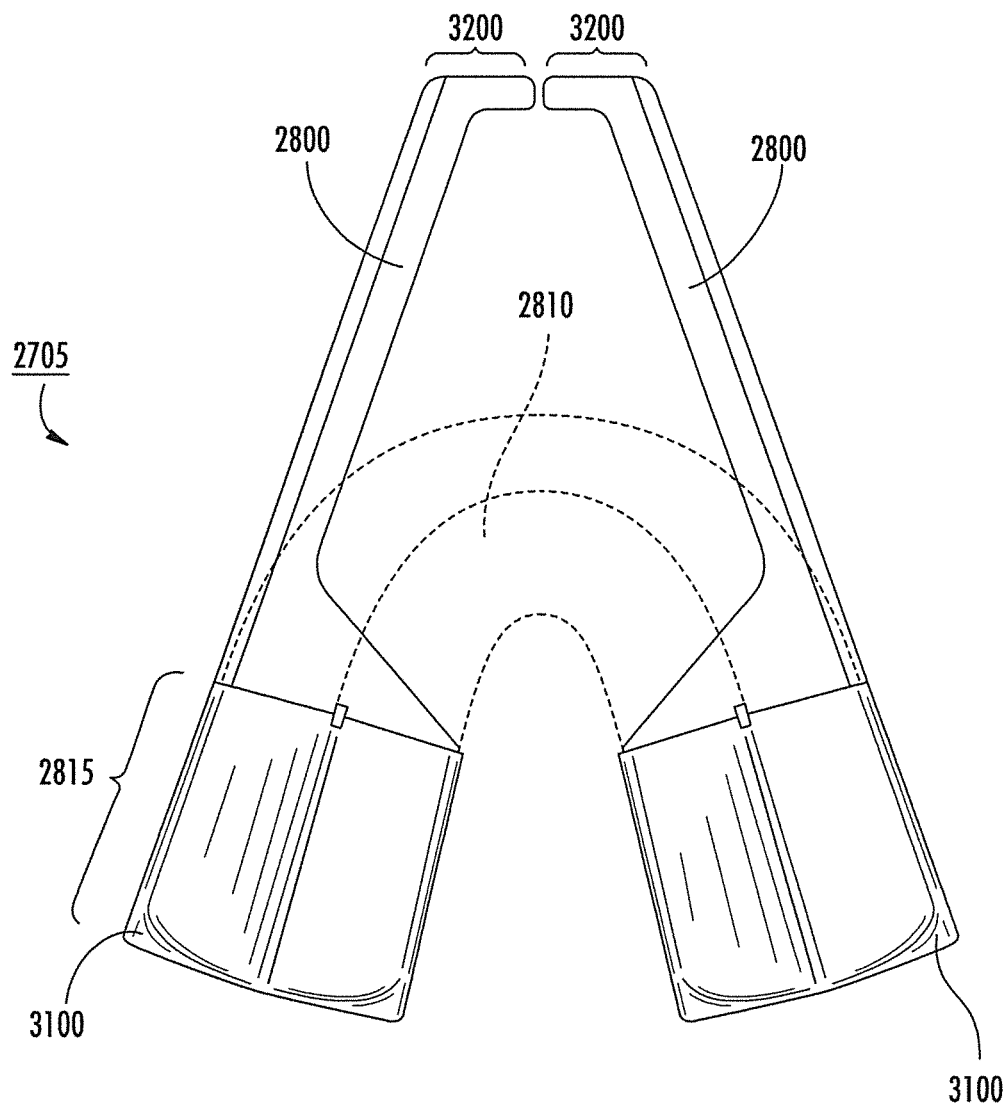
FIG. 32 illustrates a top cutaway view of a bristle strip assembly of a non-framed rigid beam mouthpiece.

FIGS. 27-30 illustrate an embodiment of a non-framed rigid beam mouthpiece 2700 utilizing an H-beam construction. As exemplified by FIGS. 31*a* and 31*b*, the substantially rigid H-beam 2800 fixedly engages the upper bristle strip 3100 and lower bristle strip 3105. In one embodiment, as exemplified by FIGS. 31*a*, 31*b*, and 32, the H-beam 2800 engages proximate the molar-contacting region at the rigid region of the bristle strips 2815. In the preferred embodiment, the rigid region 2815 is over molded over the rigid H-beam 2800. The H-beam 2800 tapers and projects outwardly from the rigid region 2815 as a relatively thin projection that terminates by turning inwardly forming a foot 3200. The foot 3200 engages the reciprocating pins 780, 782 of the gear train 700 that alternatingly press against the feet 3200 to confer motion to the bristle strips 3100, 3105.

Figure 33:
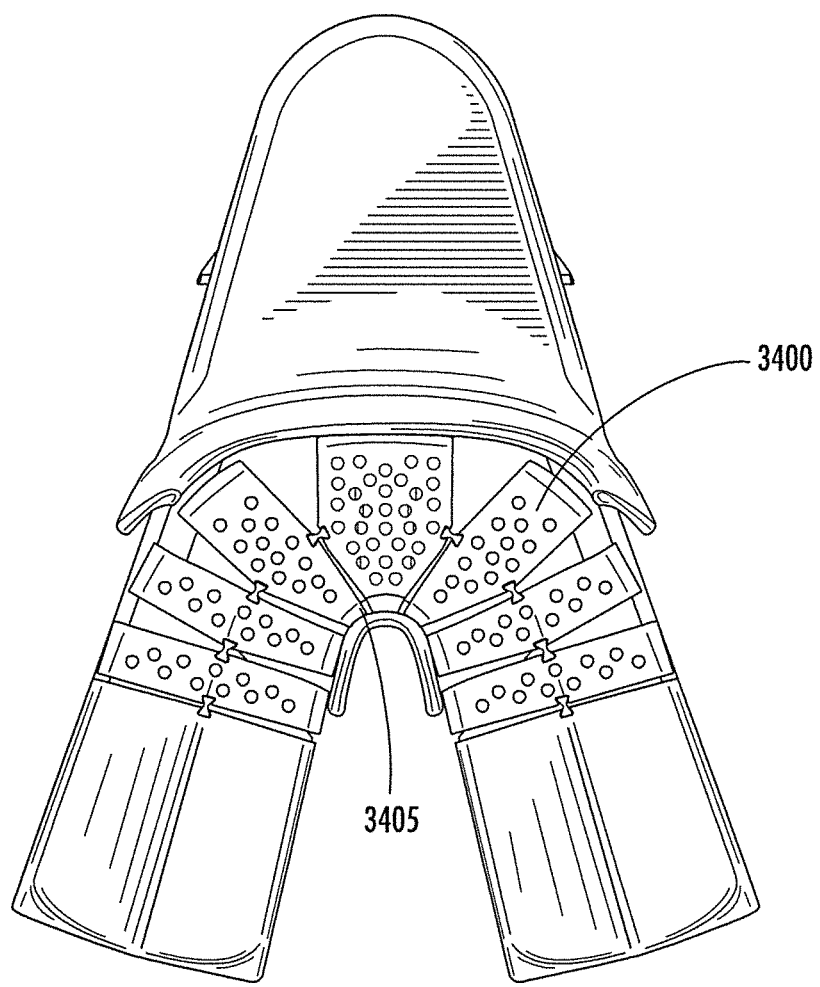
FIG. 33 illustrates a top view of a hinged bristle strip assembly of a non-framed rigid beam mouthpiece.

In a variation of the rigid beam mouthpiece 2700, as illustrated in FIGS. 33 and 34, what would have been a solid flexible region 2810 of the bristle strips 3100, 3105 is substituted with a segmented region 3400. The segmented region 3400 is constructed of a flexible or rigid material. The segmented region 3400 is of a unibody construction with a series of linked segments that each hingedly communicate with adjacent segments through hinges 3405, which are preferably living hinges. In an alternative embodiment of the segmented region 3400 hinges 3405 are constructed from overmolding. The overmolding is a flexible material so that the segmented region 3400 can hingedly move to allow the bristle strips 3100, 3105 to form substantially a U-shape and to reciprocate under actuation.

In another embodiment, the segmented region 3400 is constructed from a flexible material that is compliant enough to allow motion of the bristle strip 3100, 3105. In yet another embodiment, the hinges 3405 are separate bowtie-like shaped pieces of material that slidingly engage dovetail-shaped slots in each segment of the segmented region 3400.

Rigid Beam Mouthpiece: I-Beam

Figure 35A:
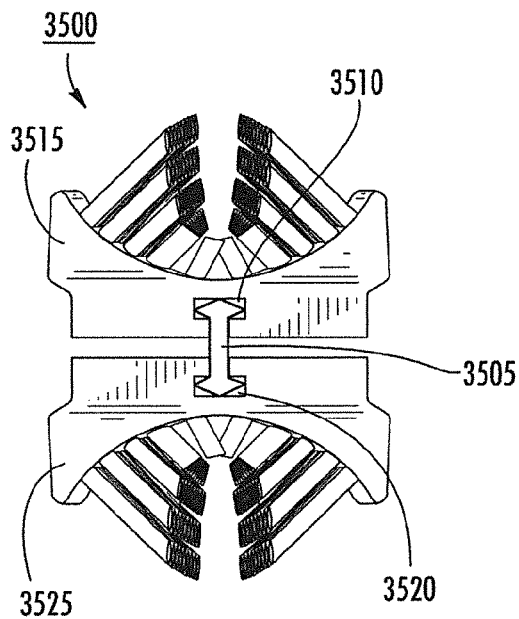
FIG. 35a illustrates a cross-sectional view of an alternative embodiment of the non-framed mouthpiece's bristle strip.
Figure 35B:
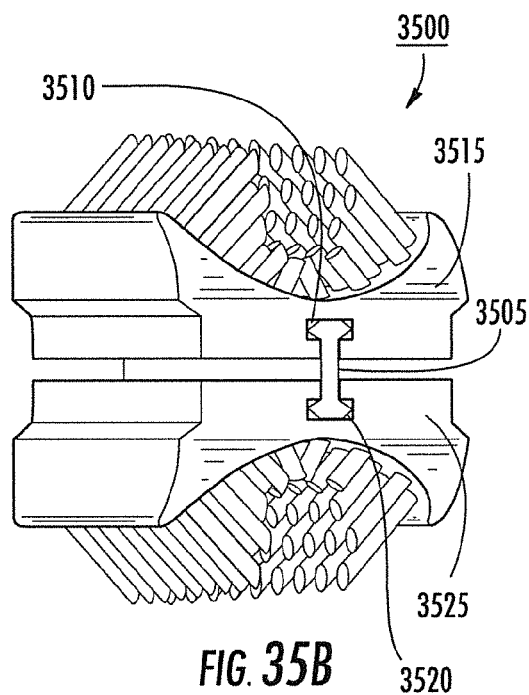

FIGS. 35*a* and 35*b* illustrate an embodiment of a rigid beam mouthpiece utilizing an I-beam construction 3500. A substantially rigid I-beam 3505 communicates with an upper t-slot 3510 in the upper bristle strip 3515 and a lower t-slot 3520 in the lower bristle strip 3525. The I-beam 3505 is made of at least one of high density polyethylene, low density polyethylene, polyethylene terephthalate, polyvinyl chloride, polypropylene, polyoxymethylene, polystyrene, post-consumer resin, K-resin, epoxy resin, phenolic formaldehyde resin, stainless steel, aluminum, ceramic, and any other material known in the art. In a preferred embodiment, the I-beam 3505 is made from a substantially non-reactive substance such as stainless steel. In one embodiment, the I-beam 3505 engages the bristle strips 3510, 3515 tightly so that minimal movement between the bristle strips 3510, 3515 and the I-beam 3505 occurs. In one embodiment, the I-beam 3505 engages the bristle strips 3510, 3515 loosely so that the bristle strips 3510, 3515 slidingly engage the I-beam 3505.

Figure 36A:
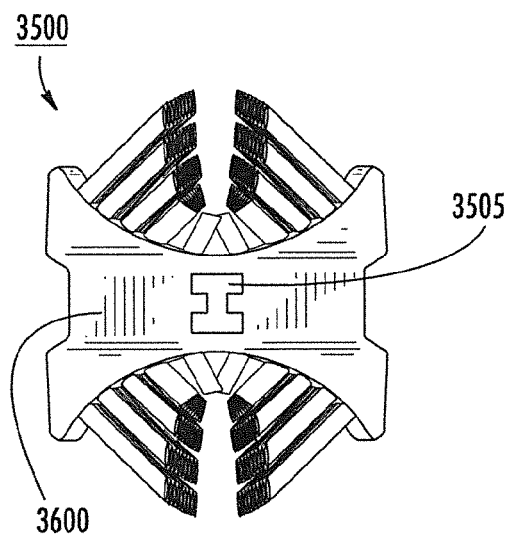
FIG. 36a illustrates a cross-sectional view of an alternative embodiment of the non-framed mouthpiece's bristle strip.
Figure 36B:
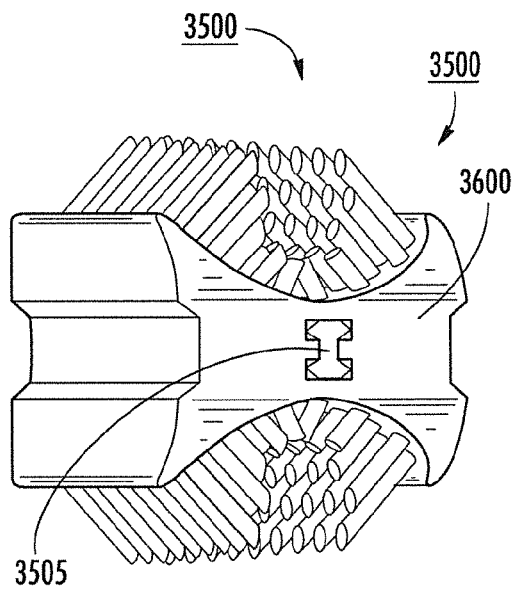

FIGS. 36*a* and 36*b* illustrate an embodiment of an I-beam construction wherein a unibody bristle strip section 3600 is of a unibody construction and the I-beam 3505 is embedded within the bristle strip 3600. This construction allows a thinner mouthpiece to be made, for the I-beam take less space than an H-beam.

Method of Use

The invention contemplates a method for brushing all of a subject's teeth simultaneously. A user would typically first charge the power supply of a rechargeable toothbrush 100 by placing the toothbrush in a charging base 225. The base 225 capable of accepting alternating current electricity and recharging a direct current power source such as a battery 340 through a wireless electrical induction circuit, or through direct circuit contact utilizing electrodes in the base 225.

Upon charging the battery 340, a user of the toothbrush 100 attaches the mouthpiece 220 to the handle 210. The mouthpiece comprises any of the bristle strip embodiments disclosed herein. The mouthpiece 220 comprises bristle strips capable of engaging all of a user's teeth simultaneously and the handle 210 comprises the battery 340 that powers a motor 350 that actuates any of the drive mechanisms 900, 1200, 1500 or the gear train 700 disclosed herein. The drive mechanisms 900, 1200, 1500 or the gear train 700 engage the bristle strips, causing a reciprocating motion of the bristle strips.

The user actuates a power control 390, typically a button or a switch, on the handle 210 of the toothbrush 100 to provide power to the motor 350 to drive the drive mechanisms 900, 1200, 1500 or the gear train 700.

The user places the mouthpiece 220 in the user's mouth so that the bristle strips engage all surfaces of all the user's teeth simultaneously. This may be accompanied by the use of toothpaste, baking soda, or mouthwash applied to the bristle strips. The user maintains contact between the user's teeth and the reciprocating bristles to clean the user's teeth, brushing all of a user's teeth simultaneously. The user actuates a power control 390 before or after placing the mouthpiece 220 in their mouth.

When the user is finished brushing their teeth, the user removes the mouthpiece 220 from their mouth and turns off the toothbrush by actuating a power control 390 to remove power from the motor 350. Alternatively, control circuitry automatically turns off the motor 350 after an appropriate amount of time has passed.

That which is claimed is:

1. A toothbrush comprising:
    an actuatable bristle strip;
    a substantially U-shaped frame of a size and dimension to fit in a user's mouth and envelope substantially all of the teeth, the frame engaging the bristle strip such that the bristle strip engages substantially all of a user's teeth simultaneously;
    an actuation means in communication with the bristle strip to actuate reciprocating movement of the bristle strip lengthwise along the frame; and
    an aperture within the frame to allow the bristle strip to communicate with the actuation means.

2. The toothbrush of claim 1 further comprising a plurality of bristles engaging the bristle strip.

3. The toothbrush of claim 1 further comprising:
a motor that engages an actuation means; and
a power source that provides power to the motor.

4. The toothbrush of claim 3 further comprising:
a handle shell that encases the motor and the power source, the handle shell engaging the U-shaped frame.

5. The toothbrush of claim 4 wherein the U-shaped frame is removable from the handle shell.

6. The toothbrush of claim 1 wherein the actuation means is a wire drive system comprising at least one wire in communication with the bristle strip and the actuation means, the wire capable of causing the bristle strip to reciprocate.

7. The toothbrush of claim 6 wherein the wire drive system includes a pulley in communication with the at least one wire and the bristle strip, the pulley in further communication with a motor assembly via a rocker linkage, wherein the at least one wire causes the bristle strip to reciprocate as reciprocating motion is applied to the pulley via the rocker linkage.

8. The toothbrush of claim 1 wherein the actuation means is a linkage drive system comprising at least one linkage in communication with the bristle strip, the linkage capable of causing the bristle strip to reciprocate.

9. The toothbrush of claim 8 wherein the linkage drive system includes a gear train comprising reciprocating pins and a pivot bar, the pivot bar in pivotable communication with the linkages and the reciprocating pins such that alternating movement of the pins against the pivot bar actuates reciprocating movement of the linkages.

10. The toothbrush of claim 8 wherein the linkage drive system includes a drive wheel and a pivot bar in communication via a rocker linkage, the pivot bar in pivotable communication with the at least one linkage such that the at least one linkage actuates reciprocating movement of the bristle strip as reciprocating motion is applied to the pivot bar via the rocker linkage as the drive wheel rotates.

11. The toothbrush of claim 1 wherein the bristle strip is made of a flexible material.

12. The toothbrush of claim 1 wherein the bristle strip comprises a plurality of segments, the segments being hingedly attached to proximate segments so to allow the bristle strip to be formed into approximately a U-shape that accommodates a user's teeth.

13. The toothbrush of claim 12 wherein the segments are attached to proximate segments with living hinges.

14. The toothbrush of claim 12 wherein the segments are attached to proximate segments with overmolded hinges.

15. A toothbrush comprising:
an actuatable bristle strip of a size and dimension to substantially engage all of a user's teeth simultaneously;
at least two rigid beams attached to the bristle strip, the rigid beams each comprising a projection extending outwardly from opposing ends of the bristle strip to engage an actuation means; and
an actuation means comprising a gear train having reciprocating pins in communication with the rigid beam projection such that the reciprocating pins actuate reciprocating movement of the bristle strip.

16. The toothbrush of claim 15 further comprising:
a motor that engages the actuation means; and
a power source that provides power to the motor.

17. The toothbrush of claim 15 wherein the rigid beam comprises an I-beam-shaped profile, wherein the I-beam is at least partially embedded in the bristle strip.

18. The toothbrush of claim 15 wherein the rigid beam comprises a track, wherein the bristle strip slidingly engages the rigid beam.

19. A toothbrush comprising:
a semi-elliptical actuatable upper bristle strip comprising an upper surface, the upper surface adapted to envelope substantially all of the upper teeth of a subject;
a plurality of bristles engaging the upper surface of the upper bristle strip;
a semi-elliptical actuatable lower bristle strip comprising a lower surface, the lower surface adapted to envelope substantially all of the lower teeth of a subject;
a plurality of bristles engaging the lower surface of the lower bristle strip; and
an actuation means in communication with the upper and lower bristle strips, the actuation means for reciprocatingly actuating the bristle strips.

20. The toothbrush of claim 19 further comprising:
a rigid beam attached to at least one of the upper or lower bristle strips, the rigid beam comprising a projection extending outwardly from the bristle strip to engage an actuation means; and
an actuation means comprising a gear train having reciprocating pins in communication with the rigid beam projection.

21. The toothbrush of claim 20 wherein the rigid beam is at least partially securely embedded in the bristle strip.

22. The toothbrush of claim 19, wherein:
the upper bristle strip comprises at least one upper t-slot proximate a distal end of the upper bristle strip;
the lower bristle strip comprises at least one lower t-slot proximate a distal end of the lower bristle strip;
the upper bristle strip communicates with the lower bristle strip through a substantially rigid I-beam, the I-beam engaging the t-slots of the bristle strips; and
the upper and lower bristle strips slidingly engage the rigid beam.

23. The toothbrush of claim 19, further comprising:
a motor assembly engaging the drive assembly; and
a power source that powers the motor assembly.

* * * * *